United States Patent [19]
James et al.

[11] Patent Number: 5,928,998
[45] Date of Patent: Jul. 27, 1999

[54] ARYLINDAZOLES AND THEIR USE AS HERBICIDES

[75] Inventors: Donald R. James, El Sobrante; Don R. Baker, Orinda; Steven D. Mielich, Palo Alto; William J. Michaely, El Cerrito, all of Calif.; Steven Fitzjohn, Bracknell, United Kingdom; Christopher G. Knudsen, Berkeley, Calif.; Christopher Mathews, San Francisco, Calif.; John M. Gerdes, Fairfax, Calif.

[73] Assignee: Zeneca Limited, London, United Kingdom

[21] Appl. No.: 08/730,632

[22] Filed: Dec. 9, 1996

Related U.S. Application Data

[60] Continuation of application No. 08/348,263, Nov. 30, 1994, abandoned, which is a division of application No. 08/018,871, Mar. 2, 1993, Pat. No. 5,444,038, which is a continuation-in-part of application No. 07/848,622, Mar. 9, 1992, abandoned.

[51] Int. Cl.$^6$ .......................... C07D 231/56; A01N 43/57
[52] U.S. Cl. ....................... 504/281; 504/282; 548/361.1; 548/361.5; 548/362.5
[58] Field of Search ............... 548/361.1, 361.5, 548/362.5; 504/281, 282

[56] References Cited

U.S. PATENT DOCUMENTS

| | | | |
|---|---|---|---|
| 3,647,819 | 3/1972 | Kirchner | 548/361.1 |
| 3,711,610 | 1/1973 | Kirchner | 514/406 |
| 5,266,556 | 11/1993 | Enomoto et al. | 504/281 |
| 5,444,038 | 8/1995 | James et al. | 504/253 |

*Primary Examiner*—Alan L. Rotman
*Attorney, Agent, or Firm*—Dianne Burkhard

[57] ABSTRACT

Substituted arylindazoles of the formula:

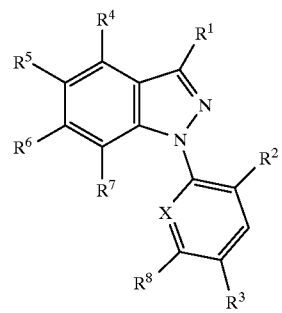

wherein X is $CR^{14}$ and $R^{14}$ is hydrogen, halogen, haloalkyl, cyano, nitro, alkylthio, alkylsulfonyl, alkylsulfinyl or alkoxy; and substituents $R^1$, $R^2$, $R^3$, $R^4$, $R^5$, $R^6$, $R^7$ and $R^8$ are as defined in the specification. Use of the compounds as herbicides and methods of making the compounds are also described.

46 Claims, No Drawings

ARYLINDAZOLES AND THEIR USE AS HERBICIDES

This application is a continuation of application Ser. No. 08/348,263 filed Nov. 30, 1994, now abandoned, which is a division of application number 08/018,871, filed Mar. 2, 1993, now U.S. Pat. No. 5,444,038, which in turn is a continuation-in-part of application Ser. No. 07/848,622, filed Mar. 9, 1992, now abandoned.

BACKGROUND AND SUMMARY OF THE INVENTION

This invention relates to substituted aryl indazoles, a process for producing them and their use as herbicides. In particular this invention relates to substituted aryl indazoles of the formula

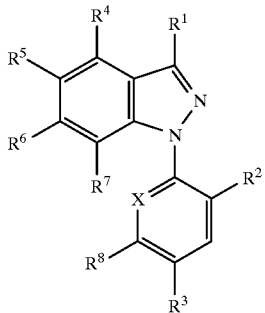

wherein $R^1$ is hydrogen or halogen;

$R^2$ is hydrogen; nitro; halogen; alkyl; cyano; alkylthio; alkylsulfinyl; alkylsulfonyl; alkoxy; acetylamino; or amino;

$R^3$ is hydrogen; halogen; haloalkyl; haloalkoxy; cyano; amino or $SO_yR^{13}$ and $R^{13}$ is alkyl or haloalkyl and y is 0, 1, or 2;

$R^4$, $R^5$ and $R^6$ are independently hydrogen; halogen; nitro; amino; hydroxy; cyano; alkyl; alkoxyiminoalkyl; hydroxyalkyl; alkoxyalkyl; alkylsulfonylaminoalkyl; haloalkylsulfonylaminoalkyl; (alkyl)$_n$aminoalkyl; (alkylcarbonyloxy)$_z$alkyl; haloalkyl; formyl; alkylcarbonyl; carboxy and its salts; COOalkyl; carboxamido; substituted carboxamido wherein the nitrogen substituents can be selected from hydrogen, alkyl, haloalkylsulfonyl, and alkylsulfonyl; sulfonamido wherein the nitrogen substituents can be selected from hydrogen and alkyl; (alkylsulfonyl)$_z$amino; (acetyl)$_z$amino;

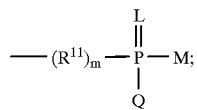

wherein L, M, P and Q are as described below;

YR9 wherein Y is O, $NR^{12}$, or $S(O)_n$; $R^9$ is $(R^{11})_m$—$COR^{10}$; —$(R^{11})_m$—$SO_2R^{10}$;

—$(R^{11})_m$—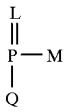—M;

alkyl; hydroxyalkyl; hydroxyalkyl aralkyl; cyanoalkyl; acetoxyalkyl; alkoxyalkyl; alkenyl; or alkynyl;

$R^{10}$ is alkyl; haloalkyl; hydrogen; hydroxy; alkoxy; alkoxyalkyl; alkoxyalkoxy; alkoxyalkylamino; dialkoxyalkylamino; aryloxy; aralkyl; alkoxycarbonyl; hydroxycarboxyl; alkoxycarbonylalkyl; hydroxycarbonylalkyl; (alkyl)$_n$amino; (alkyl)$_n$hydrazino; alkoxycarbonylalkylamino; hydroxyalkylamino; (alkyl)$_n$aminoalkylamino; (alkyl)$_n$aminocarbonylalkylamino; hydroxycarbonylalkylamino; alkylsulfonylamino; arylsulfonylamino; acetylaminoalkylamino; N-alkoxy-N-(alkyl)$_m$amino; N-hydroxy-N-(alkyl)$_m$amino; cyanoalkylamino; (alkenyl)$_n$amino; alkoxyalkylamino; (alkynyl)$_n$amino; alkenyloxy; alkynyloxy; semicarbazido; or a 5 or 6 membered heterocyclic ring comprised of CH, CH$_2$, N, O, or S;

$R^{11}$ is alkylene;

$R^{12}$ is hydrogen; alkyl; alkenyl; alkynyl or alkylcarbonyl;

M or Q is alkoxy; alkyl; (alkyl)$_n$amino; hydroxy; hydrogen; alkenyloxy; (alkenyl)$_n$amino; alkynyloxy; or (alkynyl)$_n$amino;

L is oxygen or sulfur;

P is phosphorus;

m is 0, 1;

n is 0, 1, 2;

z is 1, 2;

or $R^5$ and $R^6$ taken together with the carbon atom to which they are attached comprise an optionally substituted saturated or unsaturated heterocyclic ring having up to 6 members selected from carbon, nitrogen, oxygen and sulfur; wherein the substituents on the heterocyclic ring are defined as $R^9$ above;

$R^7$ is hydrogen; halogen; alkyl; or nitro;

$R^8$ is hydrogen or halogen;

X is nitrogen or $CR^{14}$ wherein $R^{14}$ is hydrogen; halogen; haloalkyl; cyano; nitro; alkylthio; alkylsulfonyl; alkylsulfinyl; or alkoxy;

and agriculturally acceptable salts thereof.

DESCRIPTION OF THE INVENTION

Within the scope of the above formula certain embodiments are preferred as follows:

$R^1$ is hydrogen.

$R^2$ is hydrogen, halogen, alkyl or alkylthio and more preferably hydrogen and chloro.

$R^3$ is halogen, haloalkyl, cyano, $SO_yR^{13}$ or amino, and more preferably chloro or trifluoromethyl.

$R^4$, $R^5$ and $R^6$ are independently hydrogen, cyano, halogen, C$_1$–C$_3$ alkyl, nitro, alkoxy, haloalkyl, carboxy and its salts, COOalkyl, carboxamido, substituted carboxamido, hydroxy, substituted sulfonamido, YR$^9$ wherein Y is O, NR$^{12}$, or S(O)$_n$; R$^9$ is —$(R^{11})_m$—$COR^{10}$; —$(R^{11})_m$—$SO_2R^{10}$;

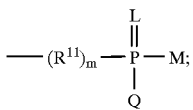

alkyl; haloalkyl; hydroxyalkyl; arylalkyl; cyanoalkyl; acetoxyalkyl; alkoxyalkyl; hydroxy; alkenyl; or alkynyl; and $R^{10}$ is hydrogen, haloalkyl, alkoxyalkyl, hydroxy, alkyl, alkoxy, alkoxyalkylamino, alkoxy, dialkoxyalkylamino, alkoxycarbonyl, alkenyloxy, and semicarbazido.

$R^7$ is hydrogen, methyl, chloro or fluoro and more preferably hydrogen.

$R^8$ is hydrogen or chloro.

$R^{11}$ is —$CH_2$—, —$CH_2CH_2$—, and —$CH(CH_3)$—.

X is N or $CR^{14}$ wherein $R^{14}$ is halogen, nitro, cyano and more preferably X is N or C-chloro.

In a preferred embodiment of the invention $R^3$ is hydrogen, halogen, $SO_yR^{13}$ and haloalkyl; $R^4$, $R^5$ and $R^6$ are independently hydrogen, halogen, alkyl, cyano, haloalkyl and $YR^9$; $R^7$ is hydrogen or halogen; $R^8$ is hydrogen or halogen and X is N or C-halogen.

In another preferred embodiment of the invention $R^3$ is hydrogen, halogen, $SO_yR^{13}$ and haloalkyl, $R^4$ is hydrogen, halogen, alkyl, cyano, haloalkyl and alkoxy; $R^5$ is hydrogen; $R^6$ is $YR^9$ wherein Y is O or $NR^{13}$ and X is N or C-halogen.

In another preferred embodiment of the invention $R^3$ is hydrogn, halogen, $SO_yR^{13}$ and haloalkyl; $R^4$ is hydrogen; and $R^5$ is hydrogen, halogen, alkyl, cyano, haloalkyl, nitro and alkoxy; $R^6$ is $YR^9$ wherein Y is O or $NR^{13}$ and X is N or C-halogen.

In another preferred embodiment $R^2$ is hydrogen or halogen; $R^3$ is hydrogen, halogen, $SO_yR^{13}$ and haloalkyl; $R^4$ is hydrogen; $R^5$ is hydrogen; $R^6$ is hydrogen, halogen, cyano, alkyl, alkoxyiminoalkyl, hydroxyalkyl, alkoxyalkyl, alkylsulfonylaminoalkyl, haloalkylsulfonylaminoalkyl, $(alkyl)_n$aminoalkyl, $(alkylcarbonyloxy)_2$alkyl, haloalkyl, formyl, alkylcarbonyl, carboxy and its salts, COOalkyl, carboxamido, substituted carboxamido wherein the nitrogen substituents can be selected from hydrogen, alkyl, haloalkylsulfonyl, and alkylsulfonyl, sulfonamido wherein the nitrogen substituents can be selected from hydrogen and alkyl, $(alkylsulfonyl)_2$amino, and $(acetyl)_2$amino and X is N or C-halogen.

In another embodiment $R^5$ and $R^6$ taken together with the carbon atom to which they are attached comprise an optionally substituted saturated or unsaturated heterocyclic ring having up to 6 members selected from C, N, O and S and X is N or C-halogen.

These embodiments are illustrative and are not meant to limit the invention in any manner.

The term "alkyl" and all groups containing alkyl portions, such as alkoxyalkyl, alkylcarbonyloxy, haloalkyl and the like, are intended to include straight-chain, branched-chain and cyclic groups. Examples are methyl, ethyl, n-propyl, isopropyl, cyclopropyl, n-butyl and t-butyl. Each acyclic alkyl member may contain one to six carbon atoms. Similarly the terms alkenyl or alkynyl refer to unsaturated or branched-chains having from two to eight carbon atoms. Alkylidene members or components of members may contain one to four carbon atoms.

The term "aryl" shall mean phenyl and other heterocyclic ring compounds, preferably pyridyl, Heterocyclic rings shall mean saturated or unsaturated rings containing at least one atom of N, O, S or P. Examples are pyridinyl, pyridazinyl, pyrimidyl, imidazolyl, furanyl, pyrrolyl, thienyl, triazolyl, oxazolyl and the like.

In the above definitions the term "halogen" includes fluoro, chloro, bromo and iodo groups. In polyhalogenated groups the halogens may be the same or different. The term "haloalkyl" refers to the alkyl group substituted by one or more halogen atoms.

Also included in the invention are the stereo and optical isomers of the compounds claimed and mixtures of these isomers in all proportions.

The compounds of the present invention, have been found to be active herbicides, possessing utility as pre-emergence and post-emergence herbicides and useful against a wide range of plant species including broadleaf and grassy species. The compounds are of particular interest when used in pre-emergence application. As mentioned hereinbelow, some of the compounds demonstrate selective control of plant species in certain crops, such as soybean, corn, rice and cotton.

This invention therefore also relates to a method for controlling undesirable vegetation comprising applying to a locus where control of such vegetation is desired, either prior or subsequent to the emergence of such vegetation, a herbicidally effective amount of a compound as described herein, together with an inert diluent or carrier suitable for use with herbicides.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions. The term "agriculturally-acceptable salt" shall mean those that readily ionize in aqueous media and includes sodium, potassium, calcium, ammonium, magnesium salts and acid salts such as hydrochloride, sulfate and nitrate.

The compounds of this invention are prepared by the following procedures.

General Method of Preparation

The unarylated indazole starting materials of the present invention can be prepared by the following two methods:

Method A: The conversion of ortho-methylanilines to indazoles by the standard diazotization-cyclization route known in the art and described in Organic Synthesis, Collective Volume III, page 660.

In general, the aniline in glacial acetic acid is diazotized by the addition of aqueous sodium nitrite or an organic nitrite such as isoamyl nitrite in an organic solvent. The cyclization occurs slowly upon standing for several days or within several hours at the reflux temperature of the organic solvent. This process is particularly effective when $R_4$–$R_7$ is electron withdrawing.

Method B: Substituted cyclohexanones are allowed to react with amide acetal at elevated temperatures to yield 2-(substituted) aminomethylene ketones. The ketone is condensed with hydrazine hydrate in alcohol solvent under reflux to yield tetrahydroindazoles. The saturated ring is then aromatized by heating in decalin containing palladiumoncarbon as a dehydration catalyst. This process is particularly effective when $R_4$–$R_7$ is an alkyl group.

The unarylated indazoles can be further modified and substituted by a variety of known standard organic reactions, for example nitration, as found in standard textbooks such as "Advanced Organic Chemistry", 4th edition, by Jerry March, Copyright, 1992 by Wiley-Interscience.

The substituted indazole is arylated with the appropriate aryl halide to give a mixture of a target aryl indazole and a minor isomer. The isomer can be removed by various techniques including recrystallization and column chromatography.

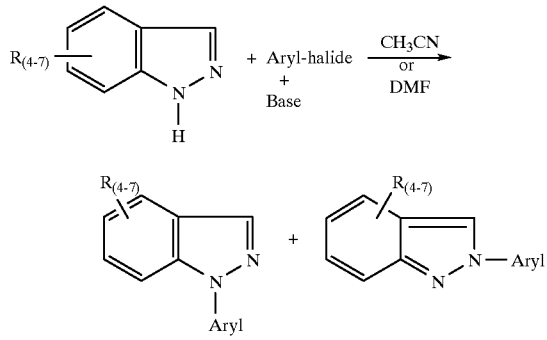

The target indazoles can additionally be prepared from ortho-halobenzaldehydes by cyclocondensation with an appropriate aryl hydrazine. The hydrazone is prepared and isolated by heating in acetonitrile for a few minutes followed by cooling. The product is cyclized by heating in an inert solvent containing a base. Temperature control is important in the final step to avoid thermal ring opening.

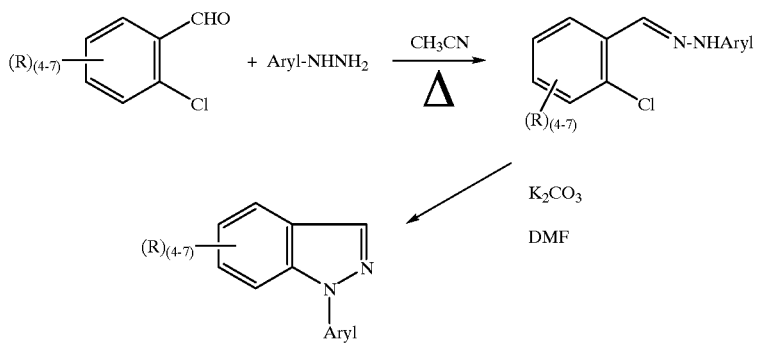

The aryl hydrazines are prepared either by standard diazotization-reduction of a substituted aniline or by displacement of an aryl halide with hydrazine (Hy).

The substituents $R^4$, $R^5$, and/or $R^6$ can be OH (which can be prepared from the methyl ether, or from the amino), SH (which can be prepared by displacing an appropriate halide or diazonium ion with mercaptide) and/or NH2 (which can be prepared by catalytically hydrogenating a nitro group). Where $R^4$, $R^5$, and/or $R^6$ are OH, SH, and/or NH2, the parent N-1-aryl-indazoles can be prepared by two general procedures. In the first method the appropriate des aryl hydroxy-, mercapto-, or aminoindazole is allowed to react with the appropriately substituted acylation or alkylation reagent in the presence of a weak base such as potassium carbonate. This product is isolated and then arylated by the appropriate haloaryl intermediate in the presence of a base. This method is exemplified in the following scheme:

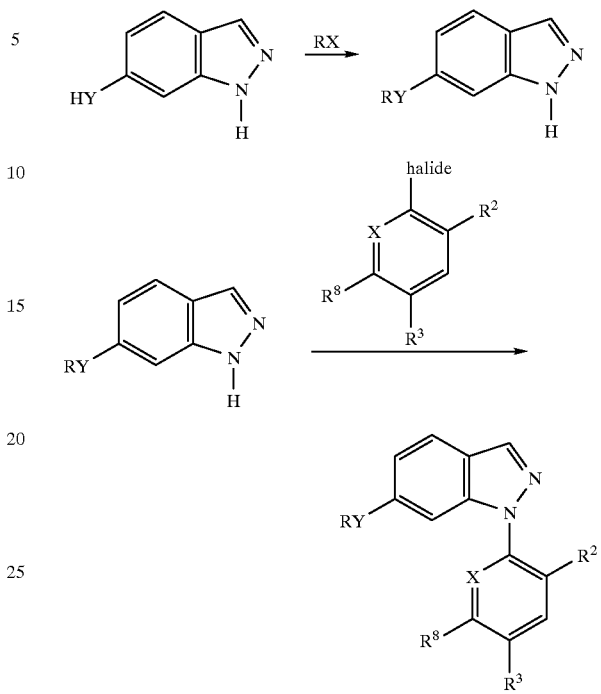

The second general method of preparation of this type of material is the reverse of the previous reaction. Here the aryl halide is allowed to react with the appropriately substituted indazole first followed by reaction of that intermediate with an alkylating or acylating reagent in the presence or of an appropriate base, or in the absence of base in the case of isocyanates and the like as follows:

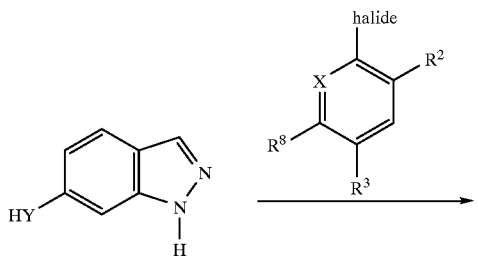

-continued

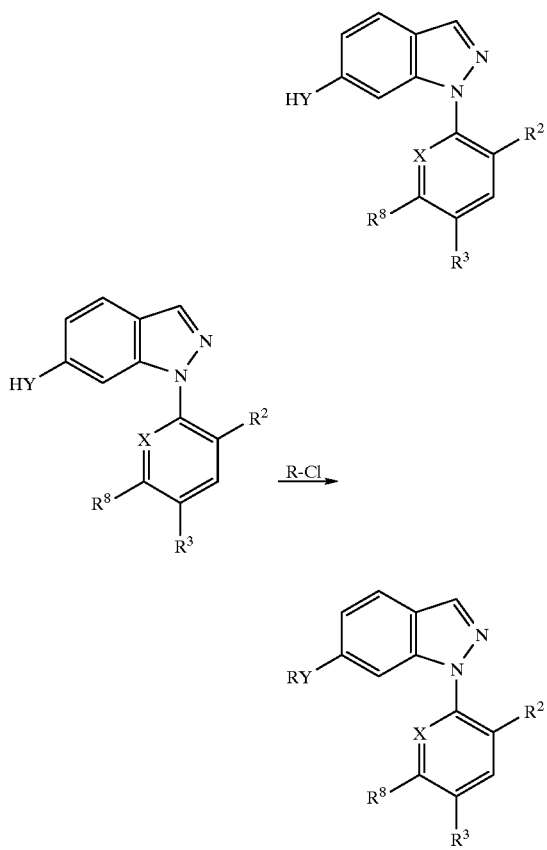

The SH, OH, and NH2 groups on the indazole ring can be alkylated, acylated and sulfonated or otherwise allowed to react with aryl isocyanates, alkyl isocyanates, acyl isocyanates or sulfonyl isocyanates to give desired products or new intermediates.

These intermediates can be further modified, using conventional methods, to create new (reactive) intermediates. For example, the ester (compound 41) can be readily hydrolyzed to the acid (compound 55) and made into its acid chloride (e.g., oxalyl chloride/DMF). This acid chloride reacts with amines, hydrazines, semicarbazine, and alcohols to give new amides (e.g. compound 91), hydrazides (e.g. compound 133), semicarbazides (e.g. compound 140), and esters (e.g. compound 154). These and other conventional methods for modification of the substituents $R^4$, $R^5$ and/or $R^6$ can be found in standard textbooks such as "Advanced Organic Chemistry", 4th edition, by Jerry March, Copyright, 1992 by Wiley-Interscience.

The following examples teach the syntheses of representative compounds of this invention. All structures are consistent with their $^1$H nuclear magnetic resonance (NMR), $^{13}$C NMR, infrared red and mass spectra:

EXAMPLE 1

1-(2,6-dichloro-4-trifluoromethylphenyl)-6-methoxy-5-nitro-1H-indazole (Compound 20 in Table I)

Preparation of the intermediate 6-methoxy-5-nitroindazole: 5-methoxy-2-methyl-4-nitroaniline (69 grams (g), 360 mmol) was mixed with 2.5 liters glacial acetic acid and stirred and cooled to about 15° C. in an ice water bath. After cooling the mixture, 25 g (360 mmol) sodium nitrite dissolved in 60 mL water was added in one portion. The resulting mixture was stirred and allowed to warm to room temperature. To allow time for complete cyclization of the diazonium salt, the solution was allowed to stand for 2 days at room temperature. The solvent was removed in vacuo at about 45° C., yielding a dark, tarry residue. The residue was purified by silica gel chromatography eluting with ethyl acetate in methylene chloride. Approximately 1 g of yellow crystals (m.p. 192–194° C.) was obtained from 5 g of residue.

Preparation of 1-(2,6-dichloro-4-trifluoromethylphenyl)-6-methoxy-5-nitro-1H-indazole: 3,5-dichloro-4-fluorobenzotrifluoride (1.2 g, 5 mmol, was mixed with a suspension of 1.0 g, (8 mmol) anhydrous, powdered potassium carbonate in 25 mL of anhydrous acetonitrile containing 0.05 g of 18-crown-6 catalyst and 6-methoxy-5-nitroindazole (0.9 g, 5 mmol) and heated under reflux for 3 hours. After cooling, the mixture was suction filtered and the filtrate was evaporated in vacuo. The residue was separated into two pure product components by silica gel chromatography eluting with ethyl acetate in hexane. The eluent yielded 1.0 g of the 1-aryl-indazole (Compound 20) and 0.2 g of the 2-arylindazole by product.

EXAMPLE 2

5-nitro-1-(2,4,6-trichlorolhenyl)-1H-indazole (Compound 3 in Table I)

Preparation of the intermediate 2-chloro-5-nitrobenzaldehyde 2,4,6-trichlorophenylhydrazone: 2,4,6-trichlorophenylhydrazine (21.0 g, 100 mmol) was dissolved in 400 mL boiling acetonitrile. To this solution was added 2-chloro-5-nitrobenzaldehyde (18.6 g, 100 mmol) in 100 mL of boiling acetonitrile. The resulting mixture produced a bright yellow paste and was allowed to cool to room temperature. The solid was collected by suction-filtration, washed with 200 mL isopropanol followed by 200 mL hexane and then air dried. The process yielded 37.2 g of the desired intermediate hydrazone as a powdery solid.

Preparation of (Compound 3): 12-chloro-5-nitrobenzaldehyde 2,4,6-trichlorophenylhydrazone (1.5 g, 4 mmol) was dissolved in 25 mL anhydrous dimethylformamide containing 0.8 g (6 mmol) of anhydrous powdered potassium carbonate and 0.05 g of 18-crown-6 catalyst and stirred overnight in a heated oil bath (80–90° C.) under a dry air atmosphere. The resulting solution was poured into 250 mL cold water and then saturated with salt to enable separation. The mixture was extracted with ethyl acetate, separated and dried with sodium sulfate. Evaporation in vacuo gave a purple oil which was purified by silica gel chromatography. The process yielded 1.2 g of a reddish crystalline solid, (93% yield) with a m.p. of 113–116° C. as the desired product.

EXAMPLE 3

1-(2,6-dichloro-4-trifluoromethylphenyl)-6-methoxy-1H-indazole (Compound 18 in Table I)

Preparation of the intermediate 6-methoxyindazole: 6-indazolol (4.8 g, 36 mmol) was dissolved in 25 mL of Dimethylformamide (DMF) and anhydrous potassium carbonate (9.95 g, 72 mmol) was added under nitrogen. Methyl iodide (5.6 g, 39 mmol) was added and after stirring for 1 hour at room temperature, the reaction mixture was poured into 350 mL of water. The resulting solid was combined with two extractions of the aqueous phase with ethyl acetate/ diethyl ether (1:1). This crude product was dried, concentrated and chromatographed on silica gel (ether/methylene chloride). A pure sample of 2.51 g (47% yield) of the 6-methoxy was obtained.

Preparation of compound 18: 6-methoxyindazole (3.83 g, 26 mmol) was dissolved in 50 mL of DMF under nitrogen. To this solution was added 3,5-dichloro-4-fluorobenzotrifluoride (6.1 g, 26 mmol) and anhydrous potassium carbonate (7.2 g, 52 mmol). After stirring at room temperature for 2 hours and at 80–95° C. for 2 hours, the cooled reaction mixture was poured into 500 mL of cold water. The aqueous phase was saturated with sodium chloride and extracted with ethyl acetate. The organic extract was washed with water, dried and concentrated to give 8.3 g of crude product purified by silica gel chromatography (ether/methylene chloride) to give 4.45 g of compound 18.

EXAMPLE 4

1-(3-chloro-5-trifluoromethyl-2-pyridyl)-6-indazolamine (Compound 22 in Table I)

Preparation of compound 22: A mixture of 6-indazolamine (2.7 g, 20 mmol), 2,3-dichloro-5-trifluoromethylpyridine (4.3 g, 20 mmol), and anhydrous potassium carbonate (5.5 g, 40 mmol) in 50 mL of DMF was heated at 80–95° C. for 4.5 hours. Work up as in Example 3 above gave 2.76 g (44% yield) of compound 22 after silica gel chromatography (ether/methylene chloride).

EXAMPLE 5

1-(3-chloro-5-trifluoromethyl-2-pyridyl)-6-indazolol (Compound 100 in Table I)

Preparation of compound 100: Potassium t-butoxide (22.4 g, 200 mmol) was added to a stirred mixture of 6-indazolol (13.4 g, 100 mmol) in 100 mL of anhydrous DMF with cooling. To this was next added 2,3-dichloro-5-trifluoromethylpyridine (12.0 mL, 86 mmol) at 4–7° C. over a period of 40 minutes. The reaction was stirred at room temperature for 2 hours and then diluted with 150 mL of diethyl ether and 200 mL of water. Crystals formed in the ether phase and were filtered off to give 11.0 g of what was identified as the 2-aryl minor isomer. The above aqueous phase was acidified with conc. hydrochloric acid and extracted with two 150 mL portions of ether. The extracts were dried over anhydrous magnesium sulfate to give an oily solid after evaporation of solvent. The residue was taken up in methylene chloride and the solution extracted with a 5% solution of sodium carbonate (twice with 100 mL portions). The carbonate extract was acidified as before and extracted with methylene chloride to give a solid after drying and evaporating as before. The solid was washed with hexane and filtered giving 3.7 g of compound 100.

EXAMPLE 6 ethyl R/S-2-[1-(2,6-dichloro-4-trifluoromethylphenyl)-1H-indazol-6-yloxy] propionate (Compound 41 in Table I)

Preparation of ethyl R/S-2-(1H-indazol-6-yloxy) propionate: ethyl 2-bromopropionate (5.5 mL, 42 mmol) was added to a stirred mixture of 6-indazolol (5.7 g, 42 mmol) and anhydrous potassium carbonate (5.8 g, 42 mmol) in 50 mL of anhydrous DMF at 10° C. The reaction was stirred for 6 hours at room temperature when a similar amount of anhydrous potassium carbonate was added and the mixture stirred for an additional 20 hours. The reaction mixture was diluted with 200 mL of ether and washed with 150 mL of water, a 5% solution of sodium carbonate (100 mL) and dried over anhydrous magnesium sulfate. The solution was filtered to remove drying agent and was evaporated in vacuo to give 8.7 g of the desired ester intermediate as an oil.

Preparation of compound 41: The above ester (8.7 g, 37 mmol) was dissolved in 100 mL of anhydrous DMF and potassium t-butoxide (4.2 g, 37 mmol) was added in one portion with stirring and cooling, keeping the temperature under 15° C. Next, 3,5-dichloro-4-fluorobenzotrifluoride (8.6 g, 37 mmol) was added with cooling at 15° C. while a mild exotherm occurred during the addition. The reaction mixture was stirred at room temperature for 5 hours an was then diluted with 200 mL of ether, washed with 150 mL of water, 100 mL of 5% hydrochloric acid, and 75 mL of 5% sodium bicarbonate solution. The organic phase was dried over anhydrous magnesium sulfate and evaporated in vacuo. The residue was flash-chromatographed on Florisil with ether to give 12.7 g of an oil which crystallized from pentane. The yield of crystalline compound 41 was 11.6 g.

EXAMPLE 7 ethyl R/S-2-[1-(2-chloro-6-methylthio-4-trifluoromethylphenyl)-1H-indazol-6-yloxy] propionate and ethyl R/S-2-[1-(2,6-bis-(dimethylthio)-4-trifluoromethylphenyl)-1H-indazol-6-yloxy]propionate (Compounds 57 and 58 in Table I)

Preparation of compounds 57 and 58: a solution of ethyl R/S-2-[1-(2-chloro-6-fluoro-4-trifluoromethylphenyl)-1H-indazol-6-yloxy]propionate (prepared in the same manner as Compound 41 above except using 3-chloro-4,5-difluorobenzotrifluoride) in anhydrous dimethylsulfoxide (DMSO) was treated with sodium methanethiolate (0.15 g, 2.1 mmol) at room temperature for 3 hours. Subsequently, additional sodium methanethiolate (0.15 g, 2.1 mmol) was added and stirring continued for 2 hours. The mixture was then partitioned between ether and water, the ether layer washed with brine, dried over magnesium sulfate, filtered and evaporated in vacuo. The residue was then purified by flash chromatography on silica gel (ether/hexane) to give 0.17 g of compound 57 followed by 0.13 g of compound 58.

EXAMPLE 8

5-bromo-1-(2,6-dichloro-4-trifluoromethylphenyl)-6-methoxy-1H-indazole (Compound 181 in Table I)

Preparation of 1-bromo-2-methoxy-5-methyl-4-nitrobenzene: a mixture of 2-methoxy-5-methyl-4-nitroaniline (20 g, 110 mmol) in 140 mL of water was heated under reflux and 48% hydrobromic acid (56 mL) was added dropwise and the mixture was heated for 20 minutes. The resulting suspension was cooled to 0° C. and treated with 40 mL of aqueous sodium nitrite (7.6 g, 110 mmol) dropwise keeping the temperature at 0° C. The suspension was added carefully dropwise to a 0° C. solution of cuprous bromide (18.1 g, 126 mmol) in 96 mL of water and 38 mL of 48% HBr. The mixture was stirred at 0° C. for 30 minutes and at room temperature for 1 hour and finally on a steam bath for 20 minutes to complete the reaction. The solid precipitate was suction filtered and dissolved in methylene chloride, washed with 400 mL of 10% sodium hydroxide, 5% sodium bisulfite, and water. The organic layer was dried, filtered, and evaporated in vacuo to give 24.9 g of dark brown solid. This was recrystallized from hexane to give 13.4 g of bromo compound.

Preparation of 4-bromo-5-methoxy-2-methylaniline: a mixture of iron powder (2.4 g, 43 mmol), 9 mL of ethanol, 7 mL of water and 0.2 mL of conc. hydrochloric acid was heated to 80° C. and the previously prepared nitro compound (2 g, 8.1 mmol) was added portionwise to just maintain reflux after the heat source was removed. After the rapid reflux had subsided, the mixture was allowed to cool to about 70° C. and was filtered through Celite which was then washed with methylene chloride. The aqueous layer was separated and washed with methylene chloride and the combined organic layers were dried, filtered and evaporated in vacuo to give 1.55 g of brown solid. This was purified by flash chromatography on silica gel (methylene chloride) to give 1.18 g (67% yield) of the aniline as a white solid.

Preparation of 5-bromo-6-methoxy-1H-indazole: a solution of the above aniline (4.93 g, 23 mmol) in 50 mL of benzene was treated with sodium acetate (1.94 g, 24 mmol) and then acetic anhydride (6.98 g, 68 mmol). The mixture was heated to reflux while a white precipitate formed in the flask. Isoamyl nitrite (4.00g, 34 mmol) in 10 mL of benzene was added dropwise to the hot solution over 20 minutes and the reddish mixture was heated overnight. After heating 20 hours, the reaction mixture was cooled and diluted with ether, washed with water, sodium bicarbonate, dried and filtered. The solvent was evaporated in vacuo to give 5.91 g of impure product. This was purified by flash chromatography on silica gel (methylene chloride) to give 3.75 g of an acetylated indazole intermediate. This was dissolved in ethanol (30 mL) containing 1 mL of conc. hydrochloric acid and the solution was heated under reflux for 4 hours. The solvent was then removed in vacuo and saturated aqueous sodium bicarbonate was added to the residue. The solid was filtered and dissolved in ethyl acetate/ether, dried, filtered and evaporated to give 3.10 g of the desired indazole intermediate.

Preparation of compound 181: a solution of the indazole (1.2 g, 5 mmol) and 3,5-dichloro-4-fluorobenzotrifluoride (1.15 g, 5 mmol) in 10 mL of anhydrous DMF containing anhydrous potassium carbonate (1.70 g, 12.3 mmol) was stirred at room temperature for 2 days. The mixture was poured into water and the precipitate was filtered off, dissolved in methylene chloride, dried, filtered and evaporated in vacuo. The solid residue weighed 1.96 g and was purified by silica gel chromatography (hexane/methylene chloride) to give 0.26 g of pure compound 181 and 1.45 g of impure product.

EXAMPLE 9

5-chloro-1-(2,6-dichloro-4-trifluoromethylphenyl)-1H-indazol-6-ol (Compound 253 in Table I)

Preparation of compound 253: a solution of 5-chloro-1-(2,6-dichloro-4-trifluoromethylphenyl)-6-methoxy-1-H-indazole (1.0 g, 3 mmol; prepared as for compound 181 in example 8 above) in 10 mL of anhydrous methylene chloride was chilled to −78° C. and boron tribromide (1.57 g, 6 mmol) was added and stirred for 1.5 hours at that low temperature. Subsequently, the solution was allowed to warm to room temperature and stir for 2 days. Additional boron tribromide (0.63 g, 2.5 mmol) was added and stirred at room temperature overnight and the mixture was cooled to −78° C. while 10 mL of methanol was added to quench the reaction. The volatile solvents and excess reagent were evaporated in vacuo and the residual solid washed with water and filtered. The solid was dissolved in ethyl acetate, dried, filtered and evaporated to give a crude product. This was purified by flash chromatography on silica gel to give, in addition to returned starting material, compound 253 (0.41 g, 43% yield).

EXAMPLE 10

6-acetoxymethyl-1-(2,6-dichloro-4-trifluoromethylphenyl)-1H-indazole (Compound 66 in Table I)

Preparation of 6-bromomethyl-1-(2,6-dichloro-4-trifluoromethylphenyl)-1H-indazole: 6-methyl-1-(2,6-dichloro-4-trifluoromethylphenyl)-1H-indazole (10 mmol) and N-bromosuccinimide (12 mmol) in 50 mL of carbon tetrachloride was heated under reflux and irradiated with a 275 watt sun lamp. After 4 hours, the reaction mixture was cooled, the succinimide was filtered off, and the solvent evaporated in vacuo to give 3.12 g of crude bromomethyl indazole.

Preparation of compound 66: the crude bromo derivative was added to potassium acetate (5g) in 50 mL of acetic acid and the solution was heated on a steam bath for 2 hours. The mixture was poured onto ice and after the ice melted, the solid was filtered and dried to give a crude product. This was purified by silica gel chromatography (pentane/methylene chloride) to give 1.6 g of compound 66.

EXAMPLE 11

1-(2,6-dichloro-4-trifluoromethylphenyl)-1H-indazole-6-carboxaldehyde and 6-bis-(acetoxy)methyl-1-(2,6-dichloro-4-trifluoromethylphenyl)-1H-indazole (Compounds 81 and 84 in Table I)

Preparation of compounds 81 and 84: 1-(2,6-di-chloro-4-trifluoromethylphenyl)-6-methyl-1H-indazole (6.4 g) was combined with a slight excess (2.2 equivalents) of N-bromosuccinimide in 50 mL of carbon tetrachloride. The mixture was heated under reflux and irradiated under a 275 watt sun lamp for 4 hours. The succinimide was removed by filtration and the solvent was evaporated in vacuo to give crude 6-dibromomethylindazole. This was added to potassium acetate (7.0 g) in 70 mL of acetic acid and the mixture was heated under reflux for 4 hours. The solution was poured onto ice and after the ice melted, the product was isolated by filtration. The crude product mixture was separated into its components by silica gel chromatography (pentane/ether/methylene chloride) to give 4.22 g of compound 81, 1.21 g of compound 66 and 0.81 g of compound 84.

EXAMPLE 12 methyl 3-[1-(2,6-dichloro-4-trifluoromethylphenyl)-1H-indazol-6-yl]propenoate (Compound 85 in Table I)

Preparation of compound 85: methyl triphenylphosphoniumacetate bromide salt (1.98 g) was suspended in 20 mL of anhydrous tetrahydrofuran while an excess of 97% sodium hydride (0.12 g) was added. After stirring at room temperature for 1 hour, the aldehyde (1.12 g) Compound 81 was added followed by 3 drops of ethanol. The reaction mixture was stirred overnight and the solid precipitate was filtered off. The solvent was evaporated from the filtrate in vacuo to give crude product. This material was purified by silica gel chromatography (methylene chloride) to give 1.07 g of compound 85.

EXAMPLE 13

1-(2,6-dichloro-4-trifluoromethylphenyl)-N,N-diethyl-1H-indazol-6-amine (Compound 230 in Table I)

Preparation of compound 230: 6-indazolamine (1.0 g, 3 mmol) in 10 mL of anhydrous DMF containing potassium carbonate (0.83 g, 6 mmol) and ethyl iodide (1.8 g, 10 mmol) was heated to 60° C. overnight. Subsequently, additional ethyl iodide (1.8 g, 10 mmol) was added to the flask and heating was continued for another 8 hours. The solution was diluted with 200 mL of brine and extracted into two portions of 100 mL of ethyl acetate. The combined organic layers were dried by passage through a short silica gel pad and evaporated. The residue was purified by flash chromatography on silica gel (10% ethyl acetate/hexane) to give 1.5 g of compound 230 as a pale yellow solid.

EXAMPLE 14

N-[1-(2,6-dichloro-4-trifluoromethylphenyl)-1H-indazol-6-yl]methanesulfonamide (Compound 40 in Table I)

Preparation of compound 40: 1-(2,6-dichloro-4-trifluoromethylphenyl)-1H-indazol-6-amine (2 g, 5 mmol; compound 21) and triethyl amine (0.59 g, 5 mmol) were dissolved in methylene chloride. Distilled methanesulfonyl chloride (0.67 g, 5 mmol) was then added dropwise at room temperature and the solution was stirred for 15–20 minutes. A yellow solid precipitate was collected by suction filtration, dissolved in ethyl acetate and the solution dried by passing through a small silica gel pad. The solvent was evaporated and the residue was purified by silica gel chromatography (20% ethyl acetate/hexane) to give 0.96 g of compound 40.

EXAMPLE 15

1-(2,6-dichloro-4-trifluoromethylphenyl)-6-methylthio-1H-indazole (Compound 79 in Table I)

Preparation of 6-methylthio-1H-indazole: 6-indazolamine (4 g, 30 mmol) was dissolved in 30 mL cold water containing 5.4 mL of conc. sulfuric acid. Upon chilling in ice, the solution became a paste and a solution of sodium nitrite (2.2 g) in 10 mL of cold water was added to the paste portionwise with constant agitation. The temperature was maintained below about 4° C. by adjusting the rate of addition of the nitrite solution. The solid paste gradually dissolved giving a reddish-brown solution. This solution was added carefully portionwise to a stirred suspension of freshly prepared cuprous methylmercaptan (35 g) in 200 mL of water at 40° C. Immediately, gas evolution was evident and addition was regulated to prevent frothing out of the container. Subsequently, the tan suspension was stirred until gas evolution ceased. The solution was suction filtered and the tan solid was washed with water and dried to give 0.9 g of intermediate.

Preparation of compound 79: the 6-methylthio-1H-indazole (0.9 g, 6 mmol) above was dissolved in anhydrous DMF containing anhydrous potassium carbonate (1.52 g, 11 mmol) and 3,5-dichloro-4-fluorobenzotrifluoride (1.3 g, 6 mmol) and stirred overnight at 60° C. The mixture was poured into cold water and the product extracted into ethyl acetate, which was dried over sodium sulfate and evaporated to give an oily residue. This was separated into two components by silica gel chromatography (5% ethyl acetate/hexane) to give 1.1 g of compound 79 and 0.1 g of the 2-aryl isomer.

EXAMPLE 16

4-chloro-1-(2,6-dichloro-4-trifluoromethylphenyl)-5-methyl-1H-indazole (Compound 211 in Table I)

Preparation of 4-chloro-5-methyl-1H-indazole: the known 3-chloro-2,4-dimethylaniline (14.9 g, 96 mmol) in 250 mL of anhydrous benzene was treated with potassium acetate (9.4 g, 96 mmol) and acetic anhydride (29.4 g, 288 mmol). This mixture was slowly heated to reflux while a precipitate formed. Subsequently, isoamyl nitrite (17 g, 144 mmol) was added rapidly to the refluxing suspension and heating was continued for 18 hours. The cooled suspension was filtered and the solid rinsed with benzene. The combined filtrates were evaporated and the solid residue was dissolved in 200 mL of ethanol containing 1 mL of conc. hydrochloric acid. This mixture was heated under reflux for 5 hours and the solvent was removed in vacuo. The solid residue was washed with 5% sodium bicarbonate and dissolved in ethyl acetate, dried over sodium sulfate and evaporated to give 9.3 g of intermediate solid.

Preparation of compound 211: the intermediate above was arylated as in example 15 above to give 1.4 g of compound 211 and 0.23 g of the 2-aryl isomer.

EXAMPLE 17 diethyl 1-(2,6-dichloro-4-trifluoromethylphenyl)-1H-indazol-5-ylphosphonate (Compound 161 in Table I)

Preparation of diethyl 1H-indazol-5-ylphosphonate: a mixture of triethyl amine (3.6 g, 36 mmol) and diethyl phosphite (5.0 g, 36 mmol) was treated with palladium tetrakis-triphenylphosphine (1.5 g, 13 mmol). To this mixture was added portionwise with stirring 1-acetyl-5-bromoindazole (8.0 g, 33 mmol). After about 4 g of the above indazole was added, 15 mL of toluene was added to dilute the reaction mixture followed by the remainder of the indazole. Subsequently, the reaction mixture was heated to 105° C. and heating continued for 5 hours. The mixture was cooled, diluted with diethyl ether and the precipitate filtered off. The filtrate was was washed with water, dried, filtered and evaporated to give a dark brown solid weighing 11.8 g. This was purified by silica gel chromatography to give 5.82 g of intermediate 1-acetylphosphonate. This intermediate was mixed with 100 mL of 10% hydrochloric acid which was then heated on a steam bath for 30 minutes. The cooled mixture was extracted with chloroform which was then dried, filtered and evaporated to give an oily solid weighing 4.83 g of the desired intermediate.

Preparation of compound 161: the diethyl indazol-5-ylphosphonate above (1.0 g, 4 mmol) was arylated as in example 15 to give 1.74 g (94% yield) of compound 161.

EXAMPLE 18

1-(2,6-dichloro-4-trifluoromethylphenyl)-1H-indazol-5-ylphosphonic acid (Compound 163 in Table I)

Preparation of compound 163: compound 161 (0.98 g, 2.1 mmol) in 10 mL of methylene chloride was chilled to 0° C. and trimethylsilyl bromide (1.6 g, 10.3 mmol) was added all at once. After stirring for 1.5 hours at 0° C. and overnight at room temperature, more trimethylsilyl bromide (0.3 g) was added and stirring was continued for 2 hours at room temperature. The excess reagent and solvent were evaporated in vacuo to give an orange oil which was triturated with water to give a white solid. The solid was collected by suction filtration and dissolved in 1 N sodium hydroxide which was then washed with methylene chloride. The alkali layer was acidified with 1M phosphoric acid and the white solid precipitate was filtered and dissolved in chloroform/methanol, dried, filtered, and evaporated to give 0.78 g of compound 163.

EXAMPLE 19 methyl 1-(2,6-dichloro-4-trifluoromethylphenyl)-5-nitro-1H-indazol-6-ylcarboxylate (Compound 242 in Table I)

Preparation of methyl 5-acetylamino-4-methyl-2-nitrobenzoate: a mixture of fuming nitric acid (8.4 g) and conc. sulfuric acid (260 g) was cooled to 0–10° C. and the known methyl 3-acetylamino-4-methylbenzoate (26.3 g, 127 mmol) was added portionwise with stirring. After stirring for several hours, the mixture was poured onto ice which subsequently melted. The product was collected by suction filtration, washed with water and dried. The solid was recrystallized from isopropanol to give 27 g of yellow powder.

Preparation of methyl 5-nitro-1H-indazol-6-ylcarboxylate: the cyclization of the above intermediate toluidide followed the procedure in example 16 above to give 4.9 g of the desired ester intermediate as an orange solid.

Preparation of compound 242: the arylation of the intermediate indazole above followed the procedure in example 16 above to give from 1.5 g of starting indazole, 1.8 g of compound 242.

EXAMPLE 20

1-(2,6-dinitro-4-trifluoromethylphenyl)-5-nitro-1H-indazole (Compound 108 in Table I)

Preparation of compound 108: a solution of 5-nitroindazole (2.0 g, 10 mmol) in 40 mL of anhydrous DMF was treated with 4-chloro-3,5-dinitrobenzotrifluoride (3.32 g, 10 mmol) and anhydrous potassium carbonate (1.7 g, 10 mmol). To this mixture was added a few crystals of 18-crown-6 catalyst and the solution heated to 40° C. for 4 hours. The mixture was cooled, diluted with methylene chloride, washed with water, 1 N hydrochloric acid, aqueous potassium carbonate, aqueous sodium hydroxide, then dried over magnesium sulfate. Evaporation and trituration of the residue with ether gave 2.75 g (57% yield) of a yellow solid.

EXAMPLE 21 ethyl 3-[1-(3-chloro-5-trifluoromethyl-2-pyridyl)-1H-indazol-6-ylamino]-3-oxopropionate (Compound 52 in Table I)

Preparation of compound 52: the intermediate aminoindazole prepared as in example 4 (3.2 g, 10 mmol) was dissolved in 50 mL of methylene chloride containing 1 mL of pyridine. To this was added ethyl malonyl chloride (1.40 mL, 11 mmol) with cooling. The reaction was exothermic and allowed to stand for one hour and then washed with 5% hydrochloric acid (50 mL), 5% sodium bicarbonate solution (50 mL), and dried over anhydrous magnesium sulfate. The dried solution was evaporated in vacuo to give 4.0 g of an oil which crystallized on standing from ether-pentane to give 2.7 g of a first crop of white solid of compound 52.

EXAMPLE 22

6-(2-acetoxyethoxy)-1-(3-chloro-5-trifluoromethyl-2-pyridyl)-1H-indazole (Compound 209 in Table I)

Preparation of 6-(2-acetoxyethoxy)-1H-indazole: a mixture was prepared of 6-Hydroxyindazole (13.4 g, 100 mmol), dimethyl formamide (100 mL), activated anhydrous potassium carbonate (13.8 g, 100 mmol), and 18-crown-6 (10 mg.). To this mixture was added 2-Bromoethyl acetate (11.0 mL, 100 mmol) dropwise with stirring at 5° C. under a nitrogen atmosphere. The reaction was stirred overnight and then diluted with 300 mL of ether and washed with water (150 mL), 5% sodium bicarbonate solution (twice with 100 mL portions), 5% sodium carbonate solution (100 mL); and dried over anhydrous magnesium sulfate. This dried solution was evaporated under high vacuum to give 3.2 g of an oil of 6-Acetoxyethoxyindazole.

Preparation of compound 209: the above intermediate product (3.2 g, 15 mmol) was dissolved in 50 mL of DMF and to this was added potassium t-butoxide (1.63 g, 15 mmol). To this was added in one portion, 2,3-Dichloro-5-trifluoromethylpyridine (2.1 mL, 15 mmol) at 5° C. with ice bath cooling. The temperature of the reaction was allowed to rise to room temperature and stand for one hour. The reaction was diluted with ether (150 mL) and washed with water (100 mL), 5% sodium bicarbonate solution (twice with 100 mL portions); and dried over anhydrous magnesium sulfate to yield after evaporation in vacuo 4.15 g of an oil of the desired product (Compound 209).

EXAMPLE 23

1-(3-chloro-5-trifluoromethyl-2-pyridyl)-6-(2-hydroxyethoxy)-1H-indazole (Compound 210 in Table I)

Preparation of compound 210: Compound 209 of Table 1 (3.02 g, 7.6 mmol) was mixed with ethanol (10 mL), water (1.0 mL), and 85% potassium hydroxide pellets (0.55 g, 8.3 mmol). The reaction mixture was stirred at room temperature for 20 hours and then evaporated in vacuo to give an oil which was taken up in methylene chloride (100 mL) and washed with water and dried over anhydrous magnesium sulfate and evaporated as before to give 2.14 g of an oil which crystallized from ether-hexane to yield 0.78 g of solid of the desired product (Compound 210).

EXAMPLE 24

R/S 2-[1-(2,6-dichloro-4-trifluoromethylphenyl)-1H-indazol-6-yloxy]propionic acid (Compound 55 in Table I)

Preparation of compound 55: compound 41 of Table 1 (4.5 g, 10 mmol) was mixed with methanol (100 mL), water (10 mL), and 85% potassium hydroxide pellets (0.73 g, 11 mmol). This mixture was stirred over the week end and then evaporated in vacuo to a glass which was taken up in water (100 mL) and washed with ether (80 mL) and acidified with conc. hydrochloric acid (0.91 mL). This acidified mixture was extracted with methylene chloride (twice with 75 mL portions) and the combined extracts dried over anhydrous magnesium sulfate with florisil. This dried extract was evaporated in vacuo to give a glass which was crystallized from ether-hexane to give a first fraction of 2.7 g of the desired product.

EXAMPLE 25 ethyl 2-[1-(2,6-dichloro-4-trifluoromethylphenyl)-1H-indazol-6-yloxy]-propionylaminoacetate (Compound 153 in Table I)

Preparation of compound 153: compound 55 of Table 1 (1.2 g, 3 mmol) was suspended in methylene chloride (10 mL) and to this was added carbonyl-di-imidazole (0.65 g, 4 mmol) in one portion with gas evolution. After 45 minutes a mixture of glycine ethyl ester hydrochloride (1.4 g, 10 mmol), methylene chloride (20 mL), and triethyl amine (1.4 mL, 10 mmol) was quickly prepared and added to the imidazole reaction in one portion. The reaction was slightly exothermic and after 15 minutes was diluted with ether (150 mL) and washed with water (100 mL), 5% sodium bicarbonate (twice with 75 mL portions); and dried over anhydrous magnesium sulfate,to give a glass on evaporation in vacuo. This crystalized from ether-hexane to yield 1.25 g of solid of the desired product.

EXAMPLE 26 ethyl R-2-[1-(3-chloro-5-trifluoromethyl-2-pyridyl)-1H-indazol-6-yloxy]propionate (Compound 255 in Table I)

Preparation of ethyl R-2-(1H-indazol-6-yloxy] propionate: a mixture consisting of 6-hydroxyindazole (6.7 g, 50 mmol), anhydrous DMF (100 mL), ethyl S-2-(methylsulfonyl)-oxypropionate, 90% (9.0 mL, 50 mmol), and anhydrous activated potassium carbonate (6.9 g, 50 mmol). The reaction was heated to 80–900° C. with stirring under an atmosphere of nitrogen for 90 minutes and cooled to room temperature and allowed to stand over the weekend. The reaction was diluted with ether (200 mL) and then washed with water (a 400 mL portion followed by a 100 mL portion), saturated sodium bicarbonate solution (100 mL), and water (100 mL); and then dried over magnesium sulfate followed by flash chromatography on florisil with ether to give 6.3 g of an oil identified as Ethyl R-2-(1H-indazol-6-yloxy)-propionate by its nuclear magnetic resonanance (NMR), infrared spectra, optical rotation, and mass spectroscopy determinations.

Preparation of compound 255: a mixture was prepared containing the above indazole compound (2.3 g, 10 mmol), 50 mL anhydrous DMF, and anhydrous activated potassium carbonate (1.1 g, 10 mmol). To this was added 2,3-dichloro-5-trifluoromethypyridine (1.4 mL, 10 mmol) cooled by an ice bath. It was stirred at ice bath temperature for one hour and at room temperature for one hour and then diluted with ether (200 mL). The mixture was washed with water (three times with 100 mL portions), dried over anhydrous magnesium sulfate and evaporated under high vacuum to yield 2.8 g of an oil identified as the desired product by its nuclear magnetic resonanance (NMR), infrared spectrum, optical rotation, and mass spectroscopy determinations.

The following Table I depicts representative compounds of this invention.

TABLE I

| Compound No. | $R^1$ | $R^2$ | $R^3$ | $R^4$ | $R^5$ | $R^6$ | $R^7$ | $R^8$ | X | Physical Constant M.P. °C. or $n_D^{30}$ |
|---|---|---|---|---|---|---|---|---|---|---|
| 1 | H | Cl | Cl | H | $NO_2$ | Cl | H | H | C—Cl | 61.0–62.0 |
| 2 | H | Cl | $CF_3$ | H | $NO_2$ | H | H | H | C—Cl | 102.0–1040 |
| 3 | H | Cl | Cl | H | $NO_2$ | H | H | H | C—Cl | 113.0–116.0 |
| 4 | H | H | Cl | H | $NO_2$ | H | H | Cl | C—Cl | 145.0–148.0 |
| 5 | H | Cl | Cl | H | $NO_2$ | Cl | H | Cl | C—Cl | 166.0–168.0 |
| 6 | H | Cl | $CF_3$ | H | $NO_2$ | $NO_2$ | H | H | C—Cl | 141.0–142.0 |
| 7 | H | Cl | $CF_3$ | H | $NO_2$ | H | H | H | C—(N) | 131.0–133.0 |
| 8 | H | H | $CF_3$ | H | $NO_2$ | H | H | H | C—(N) | — |
| 9 | H | Cl | Cl | H | H | H | H | Cl | C—Cl | 60.0–65.0 |
| 10 | H | Cl | Cl | $NO_2$ | H | H | H | H | C—Cl | — |
| 11 | H | Cl | $CF_3$ | H | $NO_2$ | H | H | H | C—Cl | 80.0–81.0 |
| 12 | H | Cl | $CF_3$ | $NO_2$ | H | H | H | H | C—Cl | — |
| 13 | Cl | Cl | $CF_3$ | H | H | H | H | H | C—Cl | 93.0–98.0 |
| 14 | H | Cl | $CF_3$ | H | $NO_2$ | $NO_2$ | H | H | C—Cl | 100.0–101.0 |
| 15 | H | Cl | $CF_3$ | H | H | Cl | H | H | C—Cl | 126.0–127.0 |
| 16 | H | Cl | $CF_3$ | H | $NO_2$ | $OCH_3$ | H | H | C—Cl | 162.0–164.0 |
| 17 | H | Cl | $CF_3$ | H | H | $OCH_3$ | H | H | C—Cl | 93.0–94.0 |
| 18 | H | Cl | $CF_3$ | H | $NO_2$ | $OCH_3$ | H | H | C—Cl | 149.0–151.0 |
| 19 | H | Cl | $CF_3$ | H | $NO_2$ | $NH_2$ | H | H | C—Cl | 215.0–216.0 |
| 20 | H | Cl | $CF_3$ | H | H | $NH_2$ | H | H | C—Cl | 61.0–63.0 |
| 21 | H | Cl | $CF_3$ | H | $NH_2$ | H | H | H | C—Cl | 222.0–223.0 |
| 22 | H | Cl | $CF_3$ | H | $NH_2$ | H | H | H | C—(N) | 143.0–144.0 |
| 23 | H | Cl | $CF_3$ | H | $NO_2$ | $NO_2$ | H | H | C—Cl | 126.0–127.0 |
| 24 | H | H | $CF_3$ | H | H | $NO_2$ | H | H | C—(N) | 112.0–113.0 |
| 25 | H | Cl | $CF_3$ | H | $NO_2$ | $NHCOCH_3$ | H | H | C—Cl | 142.0–144.0 |
| 26 | H | Cl | $CF_3$ | H | H | $NO_2$ | H | H | C—(N) | 86.0–87.0 |
| 27 | H | Cl | $CF_3$ | H | $NO_2$ | $NH_2$ | H | H | C—(N) | 154.0–155.0 |
| 28 | H | Cl | $CF_3$ | H | H | H | H | H | C—(N) | 183.0–184.0 |
| 29 | H | H | $CF_3$ | H | H | H | H | H | C—(N) | 199.0–200.0 |
| 30 | H | Cl | $CF_3$ | H | H | H | $NO_2$ | H | C—Cl | 143.0–144.0 |
| 31 | H | H | $CF_3$ | H | H | H | $NO_2$ | H | C—Cl | — |
| 32 | H | Cl | $CF_3$ | H | H | H | H | H | C—Cl | 225.0–227.0 |

TABLE I-continued

| Compound No. | R¹ | R² | R³ | R⁴ | R⁵ | R⁶ | R⁷ | R⁸ | X | Physical Constant M.P. °C. or $n_D^{30}$ |
|---|---|---|---|---|---|---|---|---|---|---|
| 33 | H | Cl | CF₃ | H | H | CH₃ | H | H | (N) | 58.0–60.0 |
| 34 | H | Cl | CF₃ | CH₃ | H | H | H | H | (N) | 41.0–45.0 |
| 35 | H | Cl | CF₃ | H | H | H | CH₃ | H | (N) | 91.0–92.0 |
| 36 | H | Cl | CF₃ | CH₃ | H | H | H | H | C—Cl | 89.0–91.0 |
| 37 | H | Cl | CF₃ | H | H | CH₃ | H | H | C—Cl | 90.0–92.0 |
| 38 | H | Cl | CF₃ | H | H | NH₂ | CH₃ | H | C—Cl | 135.0–137.0 |
| 39 | H | NO₂ | CF₃ | H | H | NHSO₂CH₃ | H | H | C—Cl | 183.0–185.0 |
| 40 | H | Cl | CF₃ | H | H | NHSO₂CH₃ | H | H | C—Cl | 170.0–172.0 |
| 41 | H | Cl | CF₃ | H | H | OCHCOOC₂H₅ \| CH₃ | H | H | C—Cl | 67.0–71.0 |
| 42 | H | F | CF₃ | H | NO₂ | H | H | H | C—Cl | 143.0–144.0 |
| 43 | H | Cl | CF₃ | H | H | OCHCOOC₂H₅ \| CH₃ | H | H | (N) | 81.0–82.0 |
| 44 | H | Cl | CF | H | H | OCH₂C≡H | H | H | C—Cl | 130.0–131.0 |
| 45 | H | F | CF₃ | H | H | OCHCOOC₂H₅ \| CH₃ | H | H | C—Cl | — |
| 46 | H | Cl | CF₃ | H | F | H | H | H | C—Cl | 71.0–72.0 |
| 47 | H | Cl | CF₃ | Cl | H | H | H | H | C—Cl | 110.0–112.0 |
| 48 | H | Cl | CF₃ | Cl | H | H | H | H | (N) | 69.0–72.0 |

TABLE I-continued
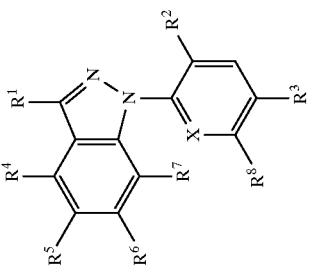
| Compound No. | R¹ | R² | R³ | R⁴ | R⁵ | R⁶ | R⁷ | R⁸ | X | Physical Constant M.P. °C. or $n_D^{3°}$ |
|---|---|---|---|---|---|---|---|---|---|---|
| 49 | H | Cl | $CF_3$ | $\underset{CH_3}{OCHCOOC_2H_5}$ | H | H | H | H | C—Cl | 87.0–89.0 |
| 50 | H | Cl | $CF_3$ | H | Br | H | H | H | (N) | — |
| 51 | H | Cl | $CF_3$ | H | H | $\underset{NHCCF_3}{\overset{O}{\|}}$ | H | H | (N) | 125.0–127.0 |
| 52 | H | Cl | $CF_3$ | H | H | $\underset{NHCCH_2C-OC_2H_5}{\overset{O\ \ \ \ \ O}{\|\ \ \ \ \ \|}}$ | H | H | (N) | 112.0–115.0 |
| 53 | H | Cl | $CF_3$ | H | H | $\underset{OCH_2C-OC_2H_5}{\overset{O}{\|}}$ | H | H | C—Cl | 90.0–92.0 |
| 54 | H | Cl | $CF_3$ | H | H | $\underset{OCH_2C-OH}{\overset{O}{\|}}$ | H | H | C—Cl | 163.0–164.0 |

TABLE I-continued

[Structure: pyrazole fused with benzene ring bearing R¹, R⁴, R⁵, R⁶, R⁷ substituents, connected via N to a pyridine/pyrazine ring (X) with R², R³, R⁸ substituents]

| Compound No. | R1 | R² | R³ | R⁴ | R⁵ | R⁶ | R⁷ | R⁸ | X | Physical Constant M.P. °C. or $n_D^{3°}$ |
|---|---|---|---|---|---|---|---|---|---|---|
| 55 | H | Cl | CF₃ | H | H | $\underset{CH_3}{\underset{\|}{OCH}}-\underset{\|}{\overset{O}{C}}-OH$ | H | H | C—Cl | 180.0–181.0 |
| 56 | H | H | H | H | NO₂ | H | H | Cl | (N) | — |
| 57 | H | SCH | CF₃ | H | H | $\underset{CH_3}{\underset{\|}{OCH}}-\underset{\|}{\overset{O}{C}}-OC_2H_5$ | H | H | C—Cl | 123.0–124.0 |
| 58 | H | SCH | CF₃ | H | H | $\underset{CH_3}{\underset{\|}{OCH}}-\underset{\|}{\overset{O}{C}}-OC_2H_5$ | H | H | C—CH₃ | 108.0–110.0 |
| 59 | H | Cl | CF₃ | H | H | NHSO₂CF₃ | H | H | (N) | 206.0–207.0 |
| 60 | H | Cl | CF₃ | H | H | $\underset{\overset{\|}{NHC}}{\overset{O}{\|}}\text{—cyclopropyl}$ | H | H | (N) | 207.0–208.0 |
| 61 | H | Cl | CF₃ | H | H | $\underset{NHC}{\overset{O}{\|}}-NHCH_3$ | H | H | (N) | 238.0–240.0 |

TABLE I-continued
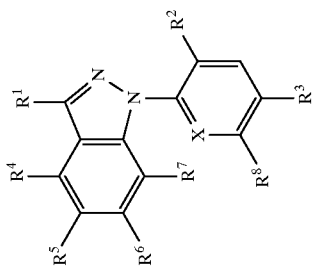
| Compound No. | R1 | R2 | R3 | R4 | R5 | R6 | R7 | R8 | X | Physical Constant M.P. °C. or $n_D^{30}$ |
|---|---|---|---|---|---|---|---|---|---|---|
| 62 | H | Cl | $CF_3$ | H | H | NHC(O)—NHCH$_2$C(O)—OC$_2$H$_5$ | H | H | (N) | 185.0–195.0 |
| 63 | H | Cl | $CF_3$ | H | H | NHC(O)—NHSO$_2$—C$_6$H$_5$ | H | H | (N) | 168.0–170.0 |
| 64 | H | Cl | $CF_3$ | H | H | NHC(O)—(CH$_2$)$_2$C(O)—OCH$_3$ | H | H | (N) | 111.0–114.0 |
| 65 | H | Cl | $CF_3$ | H | H | NHC(O)—C(O)—OC$_2$H$_5$ | H | H | (N) | 164.0–166.0 |
| 66 | H | Cl | $CF_3$ | H | H | CH$_2$OC(O)—CH$_3$ | H | H | C—Cl | 101.0–102.0 |
| 67 | H | Cl | $CF_3$ | H | C≡N | H | H | H | (N) | 92.0–93.0 |

TABLE I-continued

| Compound No. | R1 | R2 | R3 | R4 | R5 | R6 | R7 | R8 | X | Physical Constant M.P. °C. or $n_D^{30°}$ |
|---|---|---|---|---|---|---|---|---|---|---|
| 68 | H | Cl | CF$_3$ | H | H | NHC(O)—CH$_2$C(O)—OH | H | H | (N) | 150.0–151.0 |
| 69 | H | Cl | CF$_3$ | H | H | NHC(O)—CH$_2$C(O)—OC$_2$H$_5$ | H | H | C—Cl | 145.0–146.0 |
| 70 | H | Cl | CF$_3$ | H | H | NHC(O)—CH$_2$C(O)—OH | H | H | C—Cl | 165.0 (dec.) |
| 71 | H | Cl | CF$_3$ | H | H | NHC(O)—C(O)—OC$_2$H$_5$ | H | H | C—Cl | 169.0–171.0 |
| 72 | H | Cl | CF$_3$ | H | H | NHSO$_2$—CF$_3$ | H | H | C—Cl | 190.0–194.0 |
| 73 | H | Cl | CF$_3$ | H | C≡N | H | H | H | C—Cl | 88.0–90.0 |
| 74 | H | Cl | CF$_3$ | H | CH$_3$ | H | H | H | C—Cl | — |
| 75 | H | Cl | CF$_3$ | H | CH$_3$ | H | H | H | (N) | 108.0–111.0 |
| 76 | H | F | CF$_3$ | H | CH$_3$ | H | H | H | C—Cl | — |
| 77 | H | Cl | CF$_3$ | H | H | COC$_2$H$_5$(O) | H | H | C—Cl | 108.0–110.0 |

TABLE I-continued

[Structure: benzene ring fused to pyrazole (N-N) with substituents R1-R8, connected via N to a pyridine/pyrimidine ring with X, R2, R3]

| Compound No. | R$^1$ | R$^2$ | R$^3$ | R$^4$ | R$^5$ | R$^6$ | R$^7$ | R$^8$ | X | Physical Constant M.P. °C. or $n_D^{30}$ |
|---|---|---|---|---|---|---|---|---|---|---|
| 78 | H | Cl | CF$_3$ | H | H | Cl | H | H | C—Cl | 86.0–88.0 |
| 79 | H | Cl | CF$_3$ | H | H | SCH$_3$ | H | H | C—Cl | 92.0–94.0 |
| 80 | H | Cl | CF$_3$ | H | H | SO$_2$N(CH$_3$)$_2$ | H | H | C—Cl | 165.0–167.0 |
| 81 | H | Cl | CF$_3$ | H | H | CHO | H | H | C—Cl | 110.0–111.0 |
| 82 | H | H | NO$_2$ | H | NO$_2$ | H | H | H | (N) | — |
| 83 | H | NO$_2$ | NO$_2$ | H | NO$_2$ | H | H | H | (N) | — |
| 84 | H | Cl | CF$_3$ | H | H | CH—(OCHCH$_3$)$_2$ (with C=O) | H | H | C—Cl | 144.0–146.0 |
| 85 | H | Cl | CF$_3$ | H | H | CH=CHCOCH$_3$ | H | H | C—Cl | 136.0–137.0 |
| 86 | H | Cl | CF$_3$ | H | H | COH | H | H | C—Cl | 198.0–200.0 |
| 87 | H | Cl | CF$_3$ | H | H | CH=NOCH$_3$ | H | H | C—Cl | 109.0–111.0 |
| 88 | H | Cl | CF$_3$ | H | H | CH$_2$OH | H | H | C—Cl | 111.0–112.0 |
| 89 | H | Cl | CF$_3$ | H | H | N(CH$_3$)(CHCH$_3$C(O)OC$_2$H$_5$)(C(O)OC$_2$H$_5$) | H | H | C—Cl | 101.0–108.0 |

TABLE I-continued

[Structure: pyrazole fused with benzene ring bearing R1, R4, R5, R6, R7, R8 substituents, connected via N to a pyridine/pyrimidine ring with R2, R3, X substituents]

| Compound No. | R1 | R2 | R3 | R4 | R5 | R6 | R7 | R8 | X | Physical Constant M.P. °C. or $n_D^{30}$ |
|---|---|---|---|---|---|---|---|---|---|---|
| 90 | H | Cl | CF$_3$ | H | H | NHC(=O)—OCH$_3$ | H | H | C—Cl | 170.0–172.0 |
| 91 | H | Cl | CF$_3$ | H | H | OCHC(=O)—NH$_2$ | H | H | C—Cl | 178.0–179.0 |
| 92 | H | Cl | CF$_3$ | H | Cl | H | H | H | C—Cl | 83.0–89.0 |
| 93 | H | Cl | CF$_3$ | H | Cl | H | H | H | (N) | 130.0–132.0 |
| 94 | H | F | CF$_3$ | H | Cl | H | H | H | C—Cl | 75.0–76.0 |
| 95 | H | Cl | CF$_3$ | H | CH$_3$ | CH$_3$ | H | H | (N) | 101.0–102.0 |
| 96 | H | Cl | CF$_3$ | H | CH$_3$ | CH$_3$ | H | H | C—Cl | 123.0–124.0 |
| 97 | H | Cl | CF$_3$ | H | H | OCH$_3$CH=CH$_2$ | H | H | (N) | — |
| 98 | H | Cl | CF$_3$ | H | H | NHSO$_2$CH$_2$COOCH$_3$ | H | H | (N) | 56.0 (dec.) |
| 99 | H | Cl | CF$_3$ | H | H | NHSO$_2$CH$_2$CO$_2$H | H | H | (N) | 74.0–81.0 |
| 100 | H | Cl | CF$_3$ | H | H | OH | H | H | C—Cl | 153.0–155.0 |
| 101 | H | Cl | CF$_3$ | H | H | I | H | H | C—Cl | 112.0–114.0 |
| 102 | H | Cl | CF$_3$ | H | H | CH$_2$NH$_2$ | H | H | C—Cl | — |
| 103 | H | Cl | CF$_3$ | H | H | CH$_2$NHSO$_2$CF$_3$ | H | H | C—Cl | 144.0–147.0 |
| 104 | H | Cl | CF$_3$ | H | H | OCH$_2$OC$_2$H$_5$ | H | H | (N) | — |
| 105 | H | NO$_2$ | CF$_3$ | H | H | OCHCOOC$_2$H$_5$ / CH$_3$ | H | H | C—Cl | 85.0–88.0 |

TABLE I-continued

[Structure: benzindazole with R1-R8 substituents and pyridyl ring with R2, R3, X]

| Compound No. | R1 | R2 | R3 | R4 | R5 | R6 | R7 | R8 | X | Physical Constant M.P. °C. or $n_D^{30°}$ |
|---|---|---|---|---|---|---|---|---|---|---|
| 106 | H | Cl | CF$_3$ | H | H | OCHCONHCH$_3$ <br> \| <br> CH$_3$ | H | H | C—Cl | 188.0–190.0 |
| 107 | H | NO$_2$ | CF$_3$ | H | NO$_2$ | H | H | Cl | C—H | — |
| 108 | H | NO$_2$ | CF$_3$ | H | NO$_2$ | H | H | H | C—NO$_2$ | — |
| 109 | H | NO$_2$ | CN | H | NO$_2$ | H | H | H | C—NO$_2$ | 158.0–160.0 |
| 110 | H | Cl | CF$_3$ | H | Cl | NO$_2$ | H | H | (N) | 65.0–66.0 |
| 111 | H | Cl | CF$_3$ | H | H | CH$_2$OCH | H | H | C—Cl | — |
| 112 | H | Cl | NH$_2$ | H | H | $\underset{\parallel}{\text{O}}$ <br> NHC—NHCH$_3$ | H | H | C—Cl | — |
| 113 | H | H | CF$_3$ | H | NO$_2$ | H | H | H | C—NO$_2$ | — |
| 114 | H | Cl | CF$_3$ | H | H | $\underset{\parallel}{\text{O}}$ <br> NHC—CH$_3$ | H | H | C—Cl | 282.0–283.0 |
| 115 | H | Cl | CF$_3$ | —C(=O)—OCH$_3$ | H | H | H | H | C—Cl | — |
| 116 | I | Cl | CF$_3$ | H | H | I | H | H | C—Cl | 90.0–92.0 |
| 117 | H | Cl | CF$_3$ | H | H | F | H | H | C—Cl | 78.0–80.0 |

TABLE I-continued

Structure: pyrazole fused benzene (with R1 on pyrazole, R4-R7 on benzene ring, R8) linked via N to pyridine (X) with R2, R3, R6 substituents.

| Compound No. | R1 | R2 | R3 | R4 | R5 | R6 | R7 | R8 | X | Physical Constant M.P. °C. or $n_D^{30}$ |
|---|---|---|---|---|---|---|---|---|---|---|
| 118 | H | Cl | $CF_3$ | H | NHC(O)—$CH_3$ | H | H | H | C—Cl | 245.0–247.0 |
| 119 | H | Cl | $CF_3$ | Br | H | H | H | H | (N) | 84.0–85.0 |
| 120 | H | Cl | $CF_3$ | Br | H | H | H | H | C—Cl | 112.0–113.0 |
| 121 | H | $NO_2$ | $CF_3$ | Br | H | H | H | H | C—Cl | 135.0–136.0 |
| 122 | H | H | $CF_3$ | H | $NO_2$ | H | H | H | C—CN | — |
| 123 | H | Cl | $CF_3$ | H | H | F | H | H | (N) | 54.0–55.0 |
| 124 | H | Cl | $CF_3$ | H | H | —C(O)—$OCH_3$ | H | H | C—Cl | 136.0–137.0 |
| 125 | H | Cl | $CF_3$ | H | H | Br | H | H | C—Cl | 65.0–67.0 |
| 126 | H | Cl | $CF_3$ | H | H | Br | H | H | (N) | 93.0–94.0 |
| 127 | H | Cl | $CF_3$ | H | OCHCH$_3$—OC(O)$C_2H_5$ | H | H | H | C—Cl | — |
| 128 | H | Cl | $CF_3$ | CN | H | H | H | H | (N) | 120.0–121.0 |
| 129 | H | Cl | $CF_3$ | CN | H | H | H | H | C—Cl | 144.50 |

TABLE I-continued

| Compound No. | R1 | R2 | R3 | R4 | R5 | R6 | R7 | R8 | X | Physical Constant M.P. °C. or $n_D{}^{3°}$ |
|---|---|---|---|---|---|---|---|---|---|---|
| 130 | H | Cl | CF$_3$ | H | H | OCHC(=O)—OC$_2$H$_5$ / CH$_3$ | H | H | C—NHAc | 94.0–98.0 |
| 131 | H | Cl | CF$_3$ | H | H | NHCOCH$_3$ | H | H | (N) | 115.0–118.0 |
| 132 | H | Cl | CF$_3$ | H | H | NHCH$_2$CHCH$_2$CO$_2$H / CH$_3$ | H | H | (N) | 150 (dec.) |
| 133 | H | Cl | CF$_3$ | H | H | OCHC(=O)N(CH$_3$)$_2$ / CH$_3$ | H | H | C—Cl | 140.0–142.0 |
| 134 | H | Cl | CF$_3$ | H | H | OCHC(=O)—N(CH$_3$)$_2$ / CH$_3$ | H | H | C—Cl | 141.0–142.0 |
| 135 | H | Cl | CF$_3$ | H | H | OCHCO$_2$K / CH$_3$ | H | H | C—Cl | — |

TABLE I-continued
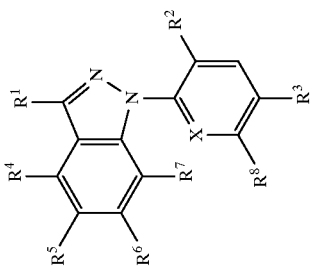
| Compound No. | R1 | R2 | R3 | R4 | R5 | R6 | R7 | R8 | X | Physical Constant M.P. °C. or $n_D^{3°}$ |
|---|---|---|---|---|---|---|---|---|---|---|
| 136 | H | Cl | CF$_3$ | H | H | OCHC(=O)CH$_3$—NHCH$_2$CH$_2$OCH$_3$ | H | H | C—Cl | 105.0–107.0 |
| 137 | H | Cl | CF$_3$ | H | H | OCHC(=O)CH$_3$NHNH$_2$ | H | H | C—Cl | 174.0–175.0 |
| 138 | H | Cl | CF$_3$ | H | H | OCHC(=O)CH$_3$—N(OCH$_3$)CH$_3$ | H | H | C—Cl | 120.0–122.0 |
| 139 | H | Cl | CF$_3$ | H | H | OCHC(=O)CH$_3$—NHN=C(CH$_3$)CH$_3$ | H | H | C—Cl | 162.0–165.0 |
| 140 | H | Cl | CF$_3$ | H | H | OCHC(=O)CH$_3$—NHNH—C(=O)—NHCH$_3$ | H | H | C—Cl | 202.0–204.0 |

TABLE I-continued

| Compound No. | R1 | R2 | R3 | R4 | R5 | R6 | R7 | R8 | X | Physical Constant M.P. °C. or $n_D^{3°}$ |
|---|---|---|---|---|---|---|---|---|---|---|
| 141 | H | Cl | CF$_3$ | H | H | OCH—C—NH—OCH$_3$ <br> \|  \|\| <br> CH$_3$  O | H | H | C—Cl | 157.0–159.0 |
| 142 | H | F | CF$_3$ | H | H | OCH$_2$C≡CH | H | H | C—Cl | 43.0–45.0 |
| 143 | H | F | CF$_3$ | H | NHSO$_2$CH$_3$ | Br | H | H | C—Cl | 57.0–59.0 |
| 144 | H | Cl | CF$_3$ | NHCOCH$_3$ | H | H | H | H | C—Cl | 180.0–181.0 |
| 145 | H | Cl | CF$_3$ | H | NO$_2$ | H | H | Cl | C—Cl | — |
| 146 | H | Cl | CF$_3$ | H | PO(OC$_2$H$_5$)$_2$ | H | H | H | (N) | — |
| 147 | H | Cl | CF$_3$ | NHSO$_2$CH$_3$ | H | H | H | H | (N) | 193.0–196.0 |
| 148 | H | Cl | CF$_3$ | N(COCH$_3$)$_2$ | H | H | H | H | C—Cl | 151.0–153.0 |
| 149 |   |   |   |   |   |   |   |   |   |   |
| 150 | H | NH$_2$ | CF$_3$ | H | H | OCHCOC$_2$H$_5$ <br> \| <br> CH$_3$ <br> ‖O | H | H | C—Cl | 153.0–155.0 |
| 151 | H | Cl | CF$_3$ | H | H | OCHC—NHCH$_2$CH$_2$CN <br> \| \|\| <br> CH$_3$ O | H | H | C—Cl | 149.0–151.0 |

TABLE I-continued
| Compound No. | R1 | R² | R³ | R⁴ | R⁵ | R⁶ | R⁷ | R⁸ | X | Physical Constant M.P. ° C. or $n_D^{3°}$ |
|---|---|---|---|---|---|---|---|---|---|---|
| 152 | H | Cl | CF₃ | H | H | OCH(CH₃)—C(=O)—NHCH₂—C(=O)—CH₃ (tetrahydrofuran-2-yl) | H | H | C—Cl | 135.0–140.0 |
| 153 | H | Cl | CF₃ | H | H | OCH(CH₃)—C(=O)—NHCH₂C(=O)—OC₂H₅ | H | H | C—Cl | 95.0–110.0 |
| 154 | H | Cl | CF₃ | H | H | OCH(CH₃)—C(=O)—O—CH₂CH₂OCH₃ | H | H | C—Cl | 66.0–68.0 |
| 155 | H | Cl | CF₃ | H | H | OCH(CH₃)—C(=O)—4-morpholinyl | H | H | C—Cl | 182.0–184.0 |
| 156 | H | Cl | CF₃ | H | H | OCH(CH₃)—C(=O)—1-pyrrolidinyl | H | H | C—Cl | 159.0–161.0 |

TABLE I-continued

| Compound No. | R1 | R2 | R3 | R4 | R5 | R6 | R7 | R8 | X | Physical Constant M.P. °C. or $n_D^{3°}$ |
|---|---|---|---|---|---|---|---|---|---|---|
| 157 | H | Cl | CF$_3$ | H | H | OCH—COCH$_2$CH$_3$<br>\|    \|\|<br>CH$_3$  O | H | H | C—Cl | 75.0–76.0 |
| 158 | H | Cl | CF$_3$ | H | CO$_2$C$_2$H$_5$ | H | H | H | C—Cl | 104.0–105.0 |
| 159 | H | Cl | CF$_3$ | H | CO$_2$H | H | H | H | C—Cl | 202.0–205.0 |
| 160 | H | Cl | CF$_3$ | H | H | OCH$_2$CCH | H | H | (N) | 75.0–76.0 |
| 161 | H | Cl | CF$_3$ | H | PO(PC$_2$H$_5$)$_2$ | H | H | H | C—Cl | 158.0–162.0 |
| 162 | H | Cl | CF$_3$ | H | NO$_2$ | OCH$_3$ | H | H | (N) | — |
| 163 | H | Cl | CF$_3$ | H | PO(OH)$_2$ | H | H | H | C—Cl | 187.0–192.0 |
| 164 | H | Cl | CF$_3$ | H | H | O<br>\|\|<br>OCHC—OCH$_3$<br>\|<br>CH$_3$ | H | H | C—Cl | 88.0–89.0 |
| 165 | H | Cl | CF$_3$ | H | H | OCHC—NHCH$_2$CH$_2$OH<br>\|    \|\|<br>CH$_3$  O | H | H | C—Cl | 97.0–102.0 |
| 166 | H | Cl | CF$_3$ | H | H | OCHC—OCH(CH$_3$)$_2$<br>\|    \|\|<br>CH$_3$  O | H | H | C—Cl | 90.0–91.0 |
| 167 | H | Cl | CF$_3$ | H | H | OCH$_3$ | H | H | (N) | 58.0–60.0 |

TABLE I-continued

| Compound No. | R1 | R2 | R3 | R4 | R5 | R6 | R7 | R8 | X | Physical Constant M.P. °C. or $n_D^{3°}$ |
|---|---|---|---|---|---|---|---|---|---|---|
| 168 | H | Cl | CF$_3$ | $\overset{O}{\underset{\|}{C}}$—OC$_2$H$_5$ | H | H | H | H | C—Cl | 82.0–85.0 |
| 169 | H | Cl | CF$_3$ | $\overset{O}{\underset{\|}{C}}$—OC$_2$H$_5$ | H | H | H | H | (N) | 70.0–72.0 |
| 170 | H | Cl | CF$_3$ | CO$_2$H | H | H | H | H | (N) | 240–243.0 |
| 171 | H | Cl | CF$_3$ | H | H | OCH—CO$_2$H $\underset{\|}{CH_3}$ | H | H | (N) | 134.0–136.0 |
| 172 | H | Cl | CF$_3$ | H | H | $\underset{CH_3}{OCH}$—$\overset{O}{\underset{\|}{C}}$—NHCH$_2$CH$_2$N(CH$_3$)$_2$ | H | H | C—Cl | — |
| 173 | H | Cl | CF$_3$ | H | H | $\underset{CH_3}{OCH}$—$\overset{}{\underset{\|}{C}}$NHCH$_2$CH$_2$NH$_2$ $\underset{}{\overset{\|}{O}}$ | H | H | C—Cl | 125.0–126.0 |

TABLE I-continued

| Compound No. | R1 | R2 | R3 | R4 | R5 | R6 | R7 | R8 | X | Physical Constant M.P. °C. or $n_D^{3°}$ |
|---|---|---|---|---|---|---|---|---|---|---|
| 174 | H | Cl | CF$_3$ | H | H | OCHC(=O)—O$^+$NH$_3$CH(CH$_3$)$_2$ \| CH$_3$ | H | H | C—Cl | 147.0–149.0 |
| 175 | H | Cl | CF$_3$ | H | H | OCHCNHCH$_2$-2-pyridyl \| CH$_3$ (C=O) | H | H | C—Cl | 138.0–139.0 |
| 176 | H | Cl | CF$_3$ | H | H | OCHC(=O)—NH$_2$ \| CH$_3$ | H | H | (N) | 180.0–181.0 |
| 177 | H | Cl | CF$_3$ | H | H | OCHC(=O)—NHCH$_2$CH$_2$OCH$_3$ \| CH$_3$ | H | H | (N) | 133.0–134.0 |
| 178 | H | Cl | CF$_3$ | H | H | OCHC(=O)—NHCH$_2$C(=O)—OC$_2$H$_5$ \| CH$_3$ | H | H | (N) | 114.0–116.0 |

TABLE I-continued

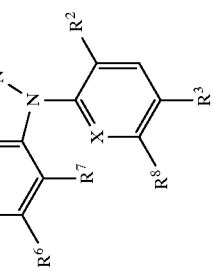

| Compound No. | R1 | R2 | R3 | R4 | R5 | R6 | R7 | R8 | X | Physical Constant M.P. °C. or $n_D^{3°}$ |
|---|---|---|---|---|---|---|---|---|---|---|
| 179 | H | Cl | CF$_3$ | H | H | OCHC—O$^+$NH$_3$CH(CH$_3$)$_2$ $\|$ $\|$ CH$_3$ O | H | H | (N) | — |
| 180 | H | Cl | CF$_3$ | H | H | OCH—C—NH—OCH$_3$ $\|$ $\|$ CH$_3$ O | H | H | (N) | 187.0–188.0 |
| 181 | H | Cl | CF$_3$ | H | Br | OCH$_3$ | H | H | C—Cl | 183.0–184.0 |
| 182 | H | Cl | CF$_3$ | H | H | OCHNHCH$_2$CH$_2$CN $\|$ $\|$ CH$_3$ O | H | H | (N) | 150.0–151.0 |
| 183 | H | Cl | CF$_3$ | H | H | OCH—NHCH$_2$—⟨tetrahydrofuran⟩ $\|$ $\|$ CH$_3$ O | H | H | (N) | 108.0–109.0 |
| 184 | H | Cl | CF$_3$ | CO$_2$H | H | H | H | H | C—Cl | 213.0–215.0 |
| 185 | H | Cl | CF$_3$ | H | H | OCH—C—OCH$_2$CH$_2$OCH$_3$ $\|$ $\|$ CH$_3$ O | H | H | (N) | 82.0–83.0 |

TABLE I-continued

| Compound No. | R1 | R2 | R3 | R4 | R5 | R6 | R7 | R8 | X | Physical Constant M.P. °C. or $n_D^{3°}$ |
|---|---|---|---|---|---|---|---|---|---|---|
| 186 | H | Cl | CF$_3$ | H | H | OCHC-4-Morpholinyl$\underset{\underset{CH_3}{\mid}}{\overset{\overset{O}{\parallel}}{}}$ | H | H | (N) | 151.0–152.0 |
| 187 | H | Cl | CF$_3$ | H | H | OCHC-1-Pyrrolidinyl$\underset{\underset{CH_3}{\mid}}{\overset{\overset{O}{\parallel}}{}}$ | H | H | (N) | 132.0–133.0 |
| 188 | H | Cl | CF$_3$ | H | H | OCHC—OCH$_2$CH$_2$CH$_3$$\underset{\underset{CH_3}{\mid}}{\overset{\overset{O}{\parallel}}{}}$ | H | H | (N) | — |
| 189 | H | Cl | CF$_3$ | H | H | OCHC—OCH$_3$$\underset{\underset{CH_3}{\mid}}{\overset{\overset{O}{\parallel}}{}}$ | H | H | (N) | 54.0–56.0 |
| 190 | H | Cl | CF$_3$ | H | H | OCHC-NHCHC—NH$_2$$\underset{\underset{CH_3}{\mid}}{\overset{\overset{O}{\parallel}}{}}\underset{\underset{CH_3}{\mid}}{\overset{\overset{O}{\parallel}}{}}$ | H | H | (N) | 170.–175.0 |
| 191 | H | Cl | CF$_3$ | H | H | OCHC-NHCHC—OC$_2$H$_5$$\underset{\underset{CH_3}{\mid}}{\overset{\overset{O}{\parallel}}{}}\underset{\underset{CH_3}{\mid}}{\overset{\overset{O}{\parallel}}{}}$ | H | H | (N) | 96.0–98.0 |

TABLE I-continued

| Compound No. | R1 | R² | R³ | R⁴ | R⁵ | R⁶ | R⁷ | R⁸ | X | Physical Constant M.P. ° C. or $n_D^{3°}$ |
|---|---|---|---|---|---|---|---|---|---|---|
| 192 | H | Cl | CF₃ | H | H | OCHC—NHCH₂CNH₂, with ∥O below C, CH₃ below CH | H | H | (N) | 139.0-143.0 |
| 193 | H | Cl | CF₃ | H | H | OCHC-1-Imidazolyl, ∥O, CH₃ | H | H | (N) | 123.0-127.0 |
| 194 | H | Cl | CF₃ | H | H | OCHC—NH-3(2-ketotetrahydrothiophenyl), ∥O, CH₃ | H | H | (N) | 157.0-160.0 |
| 195 | H | Cl | CF₃ | H | H | OCHC—NH-4-Morpholinyl, ∥O, CH₃ | H | H | (N) | 220.0-222.0 |
| 196 | H | Cl | CF₃ | H | H | OCHC—NHCH₂-3-Pyridyl, ∥O, CH₃ | H | H | (N) | 155.0-156.0 |

TABLE I-continued

| Compound No. | R1 | R² | R³ | R⁴ | R⁵ | R⁶ | R⁷ | R⁸ | X | Physical Constant M.P. °C. or $n_D^{3°}$ |
|---|---|---|---|---|---|---|---|---|---|---|
| 197 | H | Cl | CF₃ | H | H | OCHC—NHCH₂CH₂—(1-methyl-2-pyrrolyl)<br>    |  |<br>   CH₃ O | H | H | (N) | 105.0–109.9 |
| 198 | H | Cl | CF₃ | H | H | OCHCNHCH₂CH-4-morpholinyl<br>  |  |<br> CH₃ O | H | H | (N) | 115.0–118.0 |
| 199 | H | Cl | CF₃ | H | H | OCH—C—(1-methyl-4-piperidinyl)<br>  |  |<br> CH₃ O | H | H | (N) | 130.0–131.0 |
| 200 | H | Cl | CF₃ | H | H | OCHC—NH—CH₂CH₂NHCOCH₃<br>  |  |<br> CH₃ O | H | H | (N) | 192.0–195.0 |
| 201 | H | Cl | CF₃ | H | H | OCHCNHCH₂CH(OCH₃)₂<br>  |  |<br> CH₃ O | H | H | (N) | 101.0–103.0 |
| 202 | H | Cl | CF₃ | H | H | OCHCNHCH₂CN<br>  |  |<br> CH₃ O | H | H | (N) | 151.0–152.0 |

TABLE I-continued

[Structure: pyrazole-fused benzene ring with R¹, R², R³, R⁴, R⁵, R⁶, R⁷, R⁸ substituents and pyridine/pyrimidine with X]

| Compound No. | R1 | R² | R³ | R⁴ | R⁵ | R⁶ | R⁷ | R⁸ | X | Physical Constant M.P. °C. or $n_D^{3°}$ |
|---|---|---|---|---|---|---|---|---|---|---|
| 203 | H | Cl | CF₃ | H | H | OCHCNH—(4 aminocarbonyl-5-imidazolyl) <br> \|       \|\|  <br> CH₃   O | H | H | (N) | 123.0–126.0 |
| 204 | H | Cl | CF₃ | CF₃ | H | H | H | H | C—Cl | 88.0–90.0 |
| 205 | H | Cl | CF₃ | CF₃ | H | H | H | H | (N) | 67.0–69.0 |
| 206 | H | Cl | CF₃ | H | H | OCHCNHNH₂ <br> \|       \|\| <br> CH₃   O | H | H | (N) | 75.0–80.0 |
| 207 | H | Cl | CF₃ | H | H | OCHCNH-5-tetrazolyl <br> \|       \|\| <br> CH₃   O | H | H | (N) | 210.0 (dec.) |
| 208 | H | Cl | CF₃ | H | H | OCHC—OC(CH₃)₃ <br> \|       \|\| <br> CH₃   O | H | H | (N) | — |
| 209 | H | Cl | CF₃ | H | H | OCH₂CH₂OCCH₃ <br>               \|\| <br>               O | H | H | (N) | — |
| 210 | H | Cl | CF₃ | H | H | OCH₂CH₂OH | H | H | (N) | 115.0–123.0 |

TABLE I-continued

| Compound No. | R¹ | R² | R³ | R⁴ | R⁵ | R⁶ | R⁷ | R⁸ | X | Physical Constant M.P. °C. or $n_D^{30}$ |
|---|---|---|---|---|---|---|---|---|---|---|
| 211 | H | Cl | CF₃ | Cl | CH₃ | H | H | H | C—Cl | 86.0–88.0 |
| 212 | H | Cl | CF₃ | Cl | CH₃ | H | H | H | (N) | 152.0–153.0 |
| 213 | H | Cl | CF₃ | H | Cl | OCH₃ | H | H | (N) | 169.0–171.0 |
| 214 | H | Cl | CF₃ | H | H | OCH—C(=O)—NOCH₃ / CH₃ | H | H | (N) | — |
| 215 | H | Cl | CF₃ | H | CHO | OCH₃ | H | H | (N) | — |
| 216 | H | Cl | CF₃ | H | Br | OCH₃ | H | H | (N) | 177.0–178.0 |
| 217 | H | Cl | CF₃ | H | H | SO₂CH₃ | H | H | C—Cl | 142.0–143.0 |
| 218 | H | Cl | CF₃ | H | H | SO₂CH₃ | H | H | (N) | 129.0–131.0 |
| 219 | H | Cl | CF₃ | H | H | OCH=C(CH₃)CH₃ | H | H | (N) | — |
| 220 | H | Cl | CF₃ | H | H | O—CH₂—(3-methoxyphenyl) | H | H | (N) | — |
| 221 | H | Cl | CF₃ | H | H | OCH₂CN | H | H | (N) | 90.0–92.0 |
| 222 | H | Cl | CF₃ | H | Cl | OCH₃ | H | H | C—Cl | 196.0–198.0 |
| 223 | H | Cl | CF₃ | H | Cl | OCH₃ | Cl | H | C—Cl | — |

TABLE I-continued

| Compound No. | R1 | R2 | R3 | R4 | R5 | R6 | R7 | R8 | X | Physical Constant M.P. °C. or $n_D^{3°}$ |
|---|---|---|---|---|---|---|---|---|---|---|
| 224 | H | Cl | CF$_3$ | H | H | OCHC(=O)-OC$_2$H$_5$ / CH$_3$ | H | H | C—Cl | — |
| 225 | H | H | CF$_3$ | H | H | NO$_2$ | H | H | C—Cl | — |
| 226 | H | Cl | CF$_3$ | H | H | OCH(CH$_3$)$_2$ | H | H | C—Cl | — |
| 227 | H | Cl | CF$_3$ | H | H | OCH(CH$_3$)$_2$ | H | H | (N) | — |
| 228 | H | H | CF$_3$ | Cl | H | H | H | H | C—Cl | 73.0–75.0 |
| 229 | H | Cl | CF$_3$ | OCH$_3$ | H | H | H | H | C—Cl | 97.0–99.0 |
| 230 | H | Cl | CF$_3$ | H | H | N(C$_2$H$_5$)$_2$ | H | H | C—Cl | 105.0–107.0 |
| 231 | H | Cl | CF$_3$ | N(C$_2$H$_5$)$_2$ | H | H | H | H | C—Cl | 73.0–75.0 |
| 232 | H | Cl | CF$_3$ | H | H | NHSO$_2$CF$_3$ | H | H | C—Cl | — |
| 233 | H | Cl | CF$_3$ | H | Cl | H | H | H | (N) | — |
| 234 | H | Cl | CF$_3$ | H | CHO | H | H | H | C—Cl | — |
| 235 | H | Cl | CF$_3$ | H | H | OCHCN / CH$_3$ | H | H | (N) | 92.0–99.0 |
| 236 | H | Cl | CF$_3$ | H | H | OCHCN / CH$_3$ | H | H | C—Cl | 85.0–91.0 |
| 237 | H | H | CF$_3$ | H | H | OCH$_3$ | H | H | C—Cl | 78.0–82.0 |
| 238 | H | Cl | CF$_3$ | H | H | CH(Br)$_2$ | H | H | C—Cl | 98.0–100.0 |
| 239 | H | H | CF$_3$ | CN | H | H | H | H | C—Cl | 149.0–150.0 |
| 240 | H | H | CF$_3$ | H | H | OCH$_3$ | H | H | C—Cl | 162.0–164.0 |
| 241 | H | Cl | CF$_3$ | H | H | Cl | H | H | (N) | — |

TABLE I-continued

| Compound No. | $R^1$ | $R^2$ | $R^3$ | $R^4$ | $R^5$ | $R^6$ | $R^7$ | $R^8$ | X | Physical Constant M.P. °C. or $n_D^{30}$ |
|---|---|---|---|---|---|---|---|---|---|---|
| 242 | H | Cl | $CF_3$ | H | $NO_2$ | $CO_2CH_3$ | H | H | C—Cl | — |
| 243 | H | Cl | $CF_3$ | H | F | $OCH_3$ | H | H | C—Cl | 128.0–130.0 |
| 244 | H | Cl | $CF_3$ | H | $CHF_2$ | H | H | H | C—Cl | 92.0–95.0 |
| 245 | H | H | $CF_3$ | H | H | OCHC(=O)OCH$_3$ / CH$_3$ | H | H | C—Cl | 99.0–101.0 |
| 246 | H | Cl | $CF_3$ | H | H | OCHCOC$_4$H$_9$-n / CH$_3$ (C=O) | H | H | (N) | — |
| 247 | H | Cl | $CF_3$ | H | H | OCHC(=O)OC$_5$H$_{11}$-n / CH$_3$ | H | H | (N) | — |
| 248 | H | Cl | $CF_3$ | H | H | NHC(=O)CH$_2$–C$_6$H$_5$ | H | H | (N) | 161.0–167.0 |
| 249 | H | Cl | $CF_3$ | H | $NO_2$ | COCH$_3$ | H | H | (N) | 138.0–139.0 |

TABLE I-continued

| Compound No. | R1 | R² | R³ | R⁴ | R⁵ | R⁶ | R⁷ | R⁸ | X | Physical Constant M.P. °C. or $n_D^{30}$ |
|---|---|---|---|---|---|---|---|---|---|---|
| 250 | H | H | CF₃ | H | NO₂ | COCH₃ | H | H | C—Cl | 164.0–165.0 |
| 251 | H | H | CF₃ | H | Cl | H | H | H | C—Cl | — |
| 252 | H | H | CF₃ | H | H | Cl | H | H | C—Cl | — |
| 253 | H | Cl | CF₃ | H | Cl | OH | H | H | C—Cl | — |
| 254 | H | Cl | CF₃ | H | H | NHC(=O)O—C₆H₅ | H | H | (N) | 132.0–135.0 |
| 255 | H | Cl | CF₃ | H | H | (R)—OCHC(=O)—OC₂H₅ with CH₃ | H | H | (N) | 80.0–82.0 |

Herbicidal Screening Tests

The compounds listed in the foregoing table were tested for herbicidal activity as follows: As one skilled in the art is aware, the results obtained in herbicidal screening tests are affected by a number of factors that are not readily controllable. Environmental conditions, such as amount of sunlight and water, soil type, soil pH, temperature and humidity, are examples of such factors. Other factors which can affect test results are the depth of planting and the application rate of the herbicide, as well as the nature of the crops being tested. Results will also vary from crop to crop and within the crop varieties.

Pre-Emergence Herbicidal Screening Test

On the day preceding treatment, seeds of several different weed species were planted in sandy loam soil in individual rows using one species per row across the width of a flat. The weeds planted were green foxtail (SETVI) (Setaria viridis), wild oat (AVEFA) (Avena futua), watergrass (ECHCG) (Echinochlea crusgalli), wild mustard (SINAR) (Brassica kaber), velvetleaf (ABUTH) (Abutilon theophrasti), annual morningglory (PHBPU) (Ipomoea purpurea) [or morningglory (IPOSS) (Ipomoca sp.)] and yellow nutsedge (CYPES) (Cyperus esculentus). Ample seeds were planted to give about 20 to 40 seedlings per row, after emergence, depending upon the size of the plants.

Solutions of the test compounds were made by weighing out 400 or 100 milligrams (mg) of the test compound into a 60 mL wide-mouth bottle, then dissolving the compound in 25 mL acetone containing 1% Tween 20® (polyoxyethylene sorbitan monolaurate emulsifier). Additional solvents, not exceeding 5 mL, were used if needed to dissolve the compound. A 20.5 mL aliquot was then taken from the solution and diluted with 25 mL of an acetone:water mixture (19:1) containing 1% Tween 20® to form a sprayable solution.

The flats were placed in a greenhouse at 21–29.5° C., and watered by sprinkling. One day after planting, the flats were sprayed with the spray solution calibrated to deliver 400L/ha. The application rate was 4.0 or 1.0 kg/ha.

The flats were then returned to the greenhouse and water daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence, stunting, malformation, chlorosis and other types of injury. The control ratings vary from 0 to 100 percent, where 0 represents no effect with growth equal to the untreated control, and 100 represents complete kill; a dash indicates that no test was performed at that level of application.

The results of the pre-emergence test are shown in Tables II and III. The dashed line (—) indicates that the herbicidal activity of a compound was not tested on that particular weed species.

TABLE II

Pre-emergence Herbicidal Activity
Application Rate - 4.0 kg/ha

| CMPD. No. | SETVI | AVEFA | ECHCG | SINAR | ABUTH | PHBPU | IPOSS | CYPES |
|---|---|---|---|---|---|---|---|---|
| 1 | 100 | 0 | 0 | 80 | 50 | 100 | — | 0 |
| 2 | 100 | 90 | 100 | 100 | 100 | 100 | — | 0 |
| 3 | 100 | 0 | 50 | 0 | 0 | 0 | — | 0 |
| 4 | 0 | 0 | 0 | 0 | 0 | 0 | — | 0 |
| 5 | 0 | 0 | 0 | 0 | 0 | 0 | — | 0 |
| 6 | 100 | 100 | 100 | 100 | 100 | 100 | — | 5 |
| 7 | 100 | 100 | 100 | 100 | 100 | 100 | — | 40 |
| 8 | 100 | 30 | 60 | 100 | 100 | 98 | — | 0 |
| 9 | 100 | 75 | 100 | 100 | 100 | 100 | — | 5 |
| 10 | 0 | 0 | 0 | 0 | 0 | 0 | — | 0 |
| 11 | 100 | 10 | 0 | 0 | 30 | 0 | — | 0 |
| 12 | 100 | 10 | 25 | 90 | 85 | 80 | — | 0 |
| 13 | 0 | 0 | 0 | 0 | 0 | 0 | — | 0 |
| 14 | 100 | 0 | 0 | 0 | 0 | 0 | — | 0 |
| 15 | 60 | 50 | 50 | 100 | 100 | 100 | — | 0 |
| 16 | 60 | 0 | 0 | 60 | 30 | 10 | — | 0 |
| 17 | 90 | 0 | 10 | 100 | 30 | 30 | — | 0 |
| 18 | 100 | 95 | 100 | 100 | 100 | 100 | — | 0 |
| 19 | 100 | 10 | 50 | 60 | 75 | 75 | — | 0 |
| 20 | 100 | 10 | 100 | 100 | 100 | 20 | — | 0 |
| 21 | 0 | 0 | 0 | 10 | 50 | 10 | — | 0 |
| 22 | 10 | 0 | 0 | 30 | 100 | 70 | — | 0 |
| 23 | 50 | 0 | 0 | 0 | 0 | 0 | — | 0 |
| 24 |  | 0 | 0 | 0 | 0 | 0 | — | 0 |
| 25 | 0 | 0 | 0 | 0 | 0 | 0 | — | 0 |
| 26 | 10 | 0 | 0 | 0 | 5 | 0 | — | 0 |
| 27 | 0 | 0 | 0 | 0 | 0 | 0 | — | 0 |
| 28 | 100 | 10 | 25 | 95 | 100 | 60 | — | 5 |
| 29 | 100 | 10 | 30 | 100 | 95 | 65 | — | 0 |
| 30 | 50 | 0 | 0 | 100 | 20 | 30 | — | 0 |
| 31 | 10 | 0 | 0 | 0 | 0 | 0 | — | 0 |
| 32 | 10 | 5 | 0 | 10 | 0 | 0 | — | 0 |
| 33 | 100 | 85 | 100 | 100 | 100 | 95 | — | 0 |
| 34 | 100 | 80 | 100 | 100 | 100 | 70 | — | 5 |

TABLE II-continued

Pre-emergence Herbicidal Activity
Application Rate - 4.0 kg/ha

| CMPD. No. | SETVI | AVEFA | ECHCG | SINAR | ABUTH | PHBPU | IPOSS | CYPES |
|---|---|---|---|---|---|---|---|---|
| 35 | 15 | 10 | 100 | 80 | 90 | 15 | — | 0 |
| 36 | 100 | 10 | 100 | 100 | 100 | 95 | — | 5 |
| 37 | 100 | 15 | 100 | 100 | 100 | 100 | — | 5 |
| 38 | 10 | 0 | 0 | 20 | 60 | 0 | — | 0 |
| 40 | 100 | 80 | 85 | 100 | 100 | 100 | — | 5 |
| 41 | 100 | 100 | 100 | 100 | 100 | 100 | — | 95 |
| 42 | 100 | 90 | 100 | 100 | 100 | 100 | — | 20 |
| 43 | 100 | 100 | 100 | 100 | 100 | — | 100 | 100 |
| 44 | 100 | 70 | 100 | 100 | 100 | — | 90 | 20 |
| 45 | 100 | 100 | 100 | 100 | 100 | — | 100 | 100 |
| 46 | 100 | 80 | 100 | 100 | 100 | — | 100 | 25 |
| 47 | 100 | 80 | 100 | 100 | 100 | — | 100 | 5 |
| 48 | 100 | 100 | 100 | 100 | 100 | — | 100 | 30 |
| 49 | 75 | 5 | 10 | 90 | 40 | — | 25 | 0 |
| 50 | 100 | 5 | 80 | 0 | 0 | — | 5 | 0 |
| 51 | 100 | 25 | 85 | 0 | 100 | — | 30 | 10 |
| 52 | 100 | 75 | 100 | 100 | 100 | — | 100 | 65 |
| 55 | 100 | 100 | 100 | 100 | 100 | — | 100 | 100 |
| 56 | 0 | 0 | 0 | 0 | 0 | — | 0 | 0 |
| 59 | 100 | 100 | 100 | 100 | 100 | — | 100 | 100 |
| 60 | 50 | 5 | 25 | 10 | 80 | — | 0 | 0 |
| 61 | 30 | 0 | 0 | 30 | 40 | — | 5 | 0 |
| 62 | 100 | 60 | 85 | 90 | 95 | — | 75 | 5 |
| 63 | 100 | 70 | 20 | 100 | 100 | — | 100 | 0 |
| 64 | 100 | 90 | 100 | 100 | 100 | — | 100 | 60 |
| 65 | 100 | 90 | 100 | 100 | 100 | — | 100 | 50 |
| 66 | 100 | 85 | 100 | 100 | 100 | — | 98 | 0 |
| 67 | 100 | 50 | 100 | 100 | 95 | — | 90 | 20 |
| 73 | 100 | 40 | 100 | 100 | 100 | — | 100 | 10 |
| 74 | 100 | 40 | 100 | 100 | 100 | — | 50 | 0 |
| 75 | 100 | 50 | 100 | 0 | 100 | — | 50 | 0 |
| 76 | 100 | 50 | 100 | 100 | 100 | — | 60 | 0 |
| 78 | 100 | 0 | 30 | 75 | 100 | — | 40 | 0 |
| 80 | 100 | 0 | 50 | 100 | 100 | — | 85 | 0 |
| 81 | 100 | 85 | 100 | 100 | 100 | — | 100 | 15 |
| 82 | 0 | 0 | 0 | 0 | 0 | — | 0 | 0 |
| 83 | 0 | 0 | 0 | 0 | 0 | — | 0 | 6 |
| 85 | 100 | 10 | 5 | 100 | 100 | — | 80 | 0 |
| 87 | 100 | 15 | 15 | 100 | 100 | — | 60 | 0 |
| 92 | 100 | 60 | 100 | 100 | 100 | — | 95 | 0 |
| 93 | 100 | 65 | 100 | 0 | 50 | — | 10 | 5 |
| 94 | 100 | 90 | 100 | 100 | 100 | — | 100 | 5 |
| 101 | 100 | 5 | 15 | 100 | 100 | — | 30 | 5 |
| 102 | 50 | 40 | 15 | 10 | 100 | — | 100 | 0 |
| 107 | 0 | 0 | 0 | 0 | 0 | — | 0 | 0 |
| 108 | 0 | 0 | 0 | 0 | 0 | — | 0 | 0 |
| 109 | 0 | 0 | 0 | 0 | 0 | — | 0 | 0 |
| 110 | 100 | 5 | 10 | 75 | 100 | — | 75 | 5 |
| 112 | 0 | 0 | 0 | 0 | 0 | — | 0 | 0 |
| 113 | 0 | 0 | 0 | 0 | 0 | — | 0 | 0 |
| 114 | 0 | 0 | 0 | 60 | 20 | — | 5 | 5 |
| 115 | 100 | 50 | 98 | 100 | 100 | — | 75 | 30 |
| 116 | 0 | 0 | 0 | 0 | 0 | — | 0 | 0 |
| 117 | 100 | 5 | 85 | 50 | 100 | — | 90 | 5 |
| 118 | 0 | 0 | 0 | 25 | 10 | — | 5 | 0 |
| 122 | 100 | 5 | 95 | 100 | 100 | — | 100 | 10 |
| 123 | 100 | 5 | 60 | 0 | 80 | — | 40 | 0 |
| 125 | 100 | 10 | 20 | 100 | 100 | — | 85 | 0 |
| 126 | 100 | 10 | 5 | 100 | 100 | — | 85 | 0 |
| 127 | 70 | 0 | 5 | 100 | 100 | — | 60 | 0 |
| 143 | 100 | 20 | 100 | 100 | 100 | — | 70 | 0 |
| 144 | 60 | 5 | 30 | 100 | 95 | — | 30 | 0 |
| 145 | 30 | 5 | 5 | 60 | 50 | — | 25 | 0 |
| 146 | 100 | 0 | 0 | 0 | 20 | — | 60 | 0 |
| 147 | 60 | 0 | 15 | 60 | 95 | — | 60 | 0 |
| 148 | 5 | 0 | 0 | 0 | 0 | — | 5 | 0 |
| 158 | 0 | 0 | 0 | 100 | 30 | — | 30 | 0 |
| 159 | 75 | 15 | 0 | 100 | 100 | — | 30 | 0 |
| 161 | 10 | 0 | 5 | 85 | 40 | — | 0 | 0 |
| 162 | 100 | 98 | 100 | 100 | 100 | — | 100 | 40 |
| 163 | 0 | 0 | 0 | 0 | 0 | — | 0 | 0 |
| 168 | 100 | 0 | 10 | 15 | 30 | — | 0 | 0 |
| 169 | 5 | 0 | 0 | 5 | 70 | — | 0 | 0 |

TABLE II-continued

Pre-emergence Herbicidal Activity
Application Rate - 4.0 kg/ha

| CMPD. No. | SETVI | AVEFA | ECHCG | SINAR | ABUTH | PHBPU | IPOSS | CYPES |
|---|---|---|---|---|---|---|---|---|
| 170 | 0 | 0 | 0 | 15 | 80 | — | 5 | 0 |
| 181 | 100 | 20 | 60 | 100 | 100 | — | 100 | 0 |
| 184 | 10 | 0 | 0 | 60 | 10 | — | 0 | 0 |
| 204 | 100 | 10 | 60 | 100 | 100 | — | 60 | 0 |
| 205 | 100 | 80 | 100 | 100 | 100 | — | 100 | 5 |
| 211 | 100 | 90 | 100 | 100 | 100 | — | 100 | 5 |
| 212 | 100 | 90 | 100 | 100 | 100 | — | 100 | 10 |
| 213 | 100 | 95 | 100 | 10 | 98 | — | 20 | 5 |
| 215 | 100 | 85 | 100 | 100 | 60 | — | 25 | 0 |
| 216 | 100 | 10 | 15 | 10 | 5 | — | 10 | 0 |
| 217 | 100 | 50 | 100 | 100 | 100 | — | 100 | 75 |
| 218 | 100 | 90 | 100 | 100 | 100 | — | 100 | 85 |
| 223 | 100 | 0 | 0 | 30 | 60 | — | 5 | 0 |
| 224 | 100 | 100 | 100 | 100 | 100 | — | 100 | 85 |
| 225 | 0 | 0 | 0 | 0 | 0 | — | 0 | 0 |
| 228 | 100 | 50 | 100 | 100 | 100 | — | 100 | 5 |
| 229 | 100 | 10 | 100 | 100 | 100 | — | 100 | 15 |
| 230 | 100 | 0 | 5 | 10 | 0 | — | 0 | 0 |
| 231 | 10 | 0 | 0 | 0 | 0 | — | 100 | 0 |
| 232 | 0 | 0 | 0 | 0 | 0 | — | 0 | 0 |
| 233 | 100 | 100 | 100 | 100 | 100 | — | 100 | 90 |
| 234 | 30 | 0 | 5 | 100 | 100 | — | 85 | 0 |
| 238 | 100 | 40 | 100 | 100 | 100 | — | 100 | 0 |
| 239 | 100 | 30 | 85 | 100 | 100 | — | 90 | 0 |
| 240 | 100 | 20 | 60 | 100 | 100 | — | 100 | 0 |
| 241 | 100 | 60 | 100 | 15 | 30 | — | 20 | 0 |
| 244 | 100 | 60 | 100 | 100 | 100 | — | 95 | 5 |
| 251 | 100 | 50 | 100 | 95 | 100 | — | 60 | 5 |
| 252 | 100 | 5 | 15 | 10 | 100 | — | 0 | 0 |

TABLE III

Pre-emergence Herbicidal Activity
Application Rate - 1.0 kg/ha

| CMPD. NO. | SETVI | AVEFA | ECHCG | SINAR | ABUTH | PHBPU | IPOSS | CYPES |
|---|---|---|---|---|---|---|---|---|
| 1 | 100 | 0 | 0 | 0 | 0 | 0 | — | 0 |
| 2 | 100 | 80 | 100 | 100 | 100 | 100 | — | 0 |
| 3 | 100 | 0 | 30 | 0 | 0 | 0 | — | 0 |
| 4 | 0 | 0 | 0 | 0 | 0 | 0 | — | 0 |
| 5 | 0 | 0 | 0 | 0 | 0 | 0 | — | 0 |
| 59 | 100 | 100 | 100 | 100 | 100 | — | 100 | 25 |
| 68 | 100 | 50 | 100 | 100 | 85 | — | 70 | 15 |
| 69 | 95 | 10 | 5 | 100 | 100 | — | 95 | 10 |
| 70 | 95 | 75 | 70 | 100 | 100 | — | 100 | 25 |
| 71 | 20 | 0 | 0 | 100 | 75 | — | 80 | 0 |
| 72 | 100 | 80 | 70 | 100 | 100 | — | 100 | 5 |
| 77 | 100 | 40 | 20 | 100 | 100 | — | 70 | 0 |
| 79 | 100 | 40 | 100 | 100 | 100 | — | 100 | 60 |
| 84 | 80 | 30 | 10 | 100 | 100 | — | 75 | 5 |
| 86 | 100 | 90 | 15 | 100 | 100 | — | 90 | 5 |
| 88 | 85 | 40 | 20 | 100 | 100 | — | 60 | 5 |
| 89 | 30 | 0 | 0 | 30 | 30 | — | 0 | 0 |
| 90 | 90 | 0 | 0 | 60 | 20 | — | 5 | 0 |
| 91 | 100 | 75 | 100 | 100 | 100 | — | 100 | 5 |
| 95 | 100 | 25 | 100 | 70 | 100 | — | 20 | 0 |
| 96 | 100 | 15 | 70 | 100 | 100 | — | 10 | 0 |
| 97 | 100 | 60 | 100 | 100 | 100 | — | 100 | 10 |
| 98 | 100 | 5 | 20 | 100 | 100 | — | 100 | 5 |
| 99 | 100 | 10 | 40 | 100 | 100 | — | 100 | 5 |
| 100 | 70 | 5 | 30 | 5 | 40 | — | 15 | 0 |
| 103 | 20 | 5 | 0 | 100 | 100 | — | 65 | 0 |
| 104 | 100 | 30 | 100 | 0 | 10 | — | 10 | 0 |
| 105 | 70 | 25 | 10 | 100 | 100 | — | 100 | 0 |
| 106 | 100 | 20 | 5 | 100 | 100 | — | 65 | 0 |
| 111 | 100 | 60 | 100 | 100 | 100 | — | 98 | 5 |
| 119 | 100 | 95 | 100 | 100 | 100 | — | 100 | 5 |
| 120 | 100 | 40 | 100 | 100 | 100 | — | 100 | 0 |

TABLE III-continued

Pre-emergence Herbicidal Activity
Application Rate - 1.0 kg/ha

| CMPD. NO. | SETVI | AVEFA | ECHCG | SINAR | ABUTH | PHBPU | IPOSS | CYPES |
|---|---|---|---|---|---|---|---|---|
| 121 | 30 | 0 | 0 | 70 | 60 | — | 15 | 0 |
| 124 | 100 | 5 | 20 | 100 | 100 | — | 100 | 0 |
| 128 | 100 | 85 | 100 | 100 | 100 | — | 100 | 15 |
| 129 | 100 | 15 | 85 | 100 | 100 | — | 100 | 0 |
| 130 | 10 | 0 | 0 | 15 | 50 | — | 50 | 0 |
| 131 | 100 | 10 | 95 | 15 | 100 | — | 80 | 0 |
| 132 | 90 | 95 | 80 | 100 | 100 | — | 70 | 20 |
| 133 | 100 | 95 | 80 | 100 | 100 | — | 100 | 25 |
| 134 | 100 | 5 | 10 | 100 | 100 | — | 100 | 0 |
| 135 | 100 | 100 | 90 | 100 | 100 | — | 100 | 60 |
| 136 | 100 | 25 | 100 | 100 | 100 | — | 100 | 0 |
| 137 | 100 | 95 | 100 | 100 | 100 | — | 100 | 15 |
| 138 | 100 | 5 | 100 | 100 | 100 | — | 100 | 0 |
| 139 | 100 | 100 | 100 | 100 | 100 | — | 100 | 30 |
| 140 | 100 | 95 | 100 | 100 | 100 | — | 100 | 25 |
| 141 | 100 | 100 | 100 | 100 | 100 | — | 100 | 20 |
| 142 | 100 | 75 | 100 | 100 | 100 | — | 100 | 5 |
| 150 | 10 | 0 | 0 | 20 | 40 | — | 5 | 0 |
| 151 | 85 | 5 | 5 | 100 | 100 | — | 40 | 0 |
| 152 | 100 | 10 | 5 | 100 | 100 | — | 30 | 0 |
| 153 | 100 | 100 | 100 | 100 | 100 | — | 100 | 60 |
| 154 | 100 | 100 | 100 | 100 | 100 | — | 100 | 90 |
| 155 | 100 | 25 | 50 | 100 | 100 | — | 40 | 0 |
| 156 | 60 | 0 | 5 | 98 | 100 | — | 40 | 0 |
| 157 | 100 | 100 | 100 | 100 | 100 | — | 100 | 70 |
| 160 | 100 | 85 | 100 | 20 | 85 | — | 40 | 10 |
| 164 | 100 | 100 | 100 | 100 | 100 | — | 100 | 90 |
| 165 | 100 | 100 | 100 | 100 | 100 | — | 100 | 75 |
| 166 | 100 | 100 | 100 | 100 | 100 | — | 100 | 80 |
| 167 | 100 | 100 | 100 | 100 | 100 | — | 85 | 15 |
| 171 | 100 | 100 | 100 | 100 | 100 | — | 100 | 95 |
| 172 | 10 | 0 | 0 | 5 | 10 | — | 5 | 0 |
| 173 | 5 | 0 | 0 | 10 | 50 | — | 10 | 0 |
| 174 | 100 | 98 | 100 | 100 | 100 | — | 100 | 80 |
| 175 | 95 | 20 | 5 | 100 | 100 | — | 100 | 0 |
| 176 | 100 | 100 | 100 | 100 | 100 | — | 100 | 60 |
| 177 | 100 | 100 | 100 | 100 | 100 | — | 60 | 30 |
| 178 | 100 | 100 | 100 | 100 | 100 | — | 100 | 80 |
| 179 | 100 | 100 | 100 | 100 | 100 | — | 100 | 60 |
| 180 | 100 | 100 | 100 | 100 | 100 | — | 100 | 80 |
| 182 | 100 | 80 | 100 | 100 | 100 | — | 60 | 0 |
| 183 | 100 | 75 | 100 | 98 | 100 | — | 40 | 40 |
| 185 | 100 | 100 | 100 | 100 | 100 | — | 100 | 95 |
| 186 | 100 | 50 | 100 | 100 | 100 | — | 70 | 10 |
| 187 | 100 | 60 | 60 | 100 | 100 | — | 40 | 15 |
| 188 | 100 | 100 | 100 | 100 | 100 | — | 100 | 95 |
| 189 | 100 | 100 | 100 | 100 | 100 | — | 100 | 98 |
| 190 | 100 | 100 | 100 | 100 | 100 | — | 100 | 85 |
| 191 | 100 | 100 | 100 | 100 | 100 | — | 90 | 75 |
| 192 | 100 | 100 | 100 | 100 | 100 | — | 100 | 75 |
| 193 | 100 | 100 | 100 | 100 | 100 | — | 100 | 98 |
| 194 | 100 | 80 | 98 | 100 | 100 | — | 100 | 50 |
| 195 | 100 | 85 | 100 | 100 | 100 | — | 100 | 40 |
| 196 | 100 | 15 | 10 | 100 | 98 | — | 10 | 5 |
| 197 | 100 | 100 | 25 | 90 | 100 | — | 66 | 5 |
| 198 | 10 | 0 | 0 | 5 | 30 | — | 10 | 0 |
| 199 | 100 | 50 | 15 | 100 | 100 | — | 5 | 5 |
| 200 | 100 | 15 | 5 | 5 | 100 | — | 15 | 0 |
| 201 | 100 | 80 | 100 | 100 | 100 | — | 70 | 50 |
| 202 | 100 | 90 | 100 | 100 | 100 | — | 80 | 40 |
| 203 | 100 | 70 | 95 | 20 | 100 | — | 60 | 25 |
| 206 | 100 | 100 | 100 | 100 | 100 | — | 100 | 75 |
| 207 | 100 | 95 | 100 | 100 | 90 | — | 100 | 70 |
| 208 | 100 | 100 | 100 | 100 | 100 | — | 100 | 80 |
| 209 | 100 | 90 | 100 | 100 | 100 | — | 95 | 70 |
| 210 | 100 | 100 | 100 | 100 | 100 | — | 100 | 90 |
| 214 | 100 | 15 | 60 | 90 | 100 | — | 60 | 15 |
| 219 | 100 | 5 | 80 | 0 | 60 | — | 0 | 0 |
| 220 | 0 | 0 | 0 | 0 | 0 | — | 0 | 0 |
| 221 | 100 | 90 | 100 | 100 | 100 | — | 65 | 50 |
| 222 | 100 | 20 | 100 | 100 | 100 | — | 30 | 0 |
| 226 | 100 | 10 | 90 | 100 | 100 | — | 50 | 0 |
| 227 | 100 | 85 | 100 | 98 | 100 | — | 100 | 0 |

TABLE III-continued

Pre-emergence Herbicidal Activity
Application Rate - 1.0 kg/ha

| CMPD. NO. | SETVI | AVEFA | ECHCG | SINAR | ABUTH | PHBPU | IPOSS | CYPES |
|---|---|---|---|---|---|---|---|---|
| 235 | 100 | 95 | 100 | 100 | 100 | — | 100 | 15 |
| 236 | 100 | 10 | 100 | 100 | 100 | — | 100 | 5 |
| 237 | 100 | 25 | 100 | 85 | 100 | — | 60 | 0 |
| 242 | 100 | 70 | 100 | 100 | 100 | — | 85 | 5 |
| 243 | 100 | 100 | 100 | 100 | 100 | — | 100 | 40 |
| 245 | 100 | 95 | 100 | 100 | 100 | — | 70 | 60 |
| 246 | 100 | 100 | 100 | 100 | 100 | — | 100 | 95 |
| 247 | 100 | 100 | 100 | 100 | 100 | — | 100 | 90 |
| 248 | 10 | 0 | 5 | 15 | 20 | — | 0 | 0 |
| 249 | 100 | 70 | 100 | 100 | 100 | — | 95 | 10 |
| 250 | 100 | 0 | 5 | 70 | 40 | — | 10 | 5 |
| 255 | 100 | 100 | 100 | 100 | 100 | — | 100 | 98 |

Post-Emergence Herbicidal Evaluation

The soil was prepared and seeded with the same varieas described for the pre-emergence test. The flats were s in the greenhouse at 21–29° C. and watered by sprinkling. The seeds of the weed species are planted 10–12 days before treatment. Watering of the treated flats was confined to the soil surface and not to the foliage of the germinated plants.

The results of the post-emergence herbicide tests are reported in Tables IV and V.

TABLE IV

Post-emergence Herbicidal Activity
Application Rate -- 4.0 kg/ha

| CMPD. NO. | SETVI | AVEFA | ECHCG | SINAR | ABUTH | PHBPU | IPOSS | CYPES |
|---|---|---|---|---|---|---|---|---|
| 1 | 100 | 0 | 0 | 90 | 100 | 100 | — | 0 |
| 2 | 100 | 80 | 100 | 100 | 100 | 100 | — | 5 |
| 3 | 100 | 0 | 50 | 50 | 100 | 100 | — | 0 |
| 4 | 100 | 0 | 0 | 20 | 0 | 0 | — | 0 |
| 5 | 10 | 0 | 10 | 10 | 0 | 0 | — | 0 |
| 6 | 100 | 60 | 30 | 100 | 100 | 100 | — | 5 |
| 7 | 95 | 60 | 100 | 100 | 100 | 100 | — | 25 |
| 8 | 30 | 0 | 0 | 70 | 100 | 100 | — | 0 |
| 9 | 100 | 30 | 60 | 40 | 100 | 100 | — | 0 |
| 10 | 0 | 0 | 0 | 50 | 25 | 0 | — | 0 |
| 11 | 70 | 10 | 10 | 50 | 80 | 90 | — | 0 |
| 12 | 80 | 1Q | 10 | 100 | 100 | 100 | — | 0 |
| 13 | 0 | 0 | 0 | 10 | 20 | 10 | — | 0 |
| 14 | 0 | 0 | 0 | 30 | 40 | 60 | — | 0 |
| 15 | 10 | 10 | 10 | 20 | 100 | 90 | — | 0 |
| 16 | 10 | 10 | 0 | 40 | 100 | 80 | — | 0 |
| 17 | 40 | 10 | 10 | 60 | 100 | 100 | — | 0 |
| 18 | 100 | 98 | 100 | 100 | 100 | 100 | — | 5 |
| 19 | 30 | 20 | 20 | 10 | 80 | 60 | — | 0 |
| 20 | 100 | 20 | 30 | 100 | 100 | 90 | — | 0 |
| 21 | 10 | 0 | 0 | 100 | 60 | 100 | — | 0 |
| 22 | 40 | 0 | 0 | 90 | 90 | 100 | — | 0 |
| 23 | 10 | 0 | 10 | 10 | 20 | 40 | — | 0 |
| 24 | 30 | 10 | 10 | 10 | 40 | 60 | — | 0 |
| 25 | 0 | 0 | 0 | 0 | 0 | 10 | — | 0 |
| 26 | 10 | 5 | 0 | 10 | 10 | 20 | — | 0 |
| 27 | 0 | 0 | 0 | 0 | 0 | 10 | — | 0 |
| 28 | 50 | 30 | 5 | 100 | 100 | 100 | — | 5 |
| 29 | 30 | 10 | 10 | 75 | 90 | 60 | — | 0 |
| 30 | 10 | 5 | 10 | 20 | 40 | 100 | — | 0 |
| 31 | 5 | 5 | 0 | 0 | 0 | 0 | — | 0 |
| 32 | 0 | 0 | 0 | 10 | 0 | 5 | — | 0 |
| 33 | 85 | 25 | 85 | 80 | 100 | 100 | — | 5 |
| 34 | 100 | 20 | 95 | 85 | 100 | 100 | — | 5 |
| 35 | 15 | 0 | 0 | 5 | 95 | 80 | — | 0 |
| 36 | 100 | 20 | 60 | 100 | 100 | 100 | — | 5 |
| 37 | 90 | 15 | 85 | 100 | 100 | 100 | — | 5 |
| 38 | 15 | 10 | 5 | 20 | 70 | 50 | — | 0 |
| 40 | 80 | 60 | 40 | 100 | 100 | 100 | — | 15 |
| 41 | 100 | 100 | 100 | 100 | 100 | 100 | — | 100 |
| 42 | 100 | 25 | 100 | 100 | 100 | 100 | — | 20 |

TABLE IV-continued

Post-emergence Herbicidal Activity
Application Rate -- 4.0 kg/ha

| CMPD. NO. | SETVI | AVEFA | ECHCG | SINAR | ABUTH | PHBPU | IPOSS | CYPES |
|---|---|---|---|---|---|---|---|---|
| 43 | 100 | 100 | 100 | 100 | 100 | — | 100 | 100 |
| 44 | 100 | 25 | 100 | 100 | 100 | — | 100 | 15 |
| 45 | 100 | 100 | 100 | 100 | 100 | — | 100 | 100 |
| 46 | 100 | 60 | 100 | 100 | 100 | — | 100 | 20 |
| 47 | 100 | 60 | 100 | 100 | 100 | — | 100 | 10 |
| 48 | 100 | 100 | 100 | 100 | 100 | — | 100 | 40 |
| 49 | 20 | 0 | 10 | 80 | 98 | — | 95 | 0 |
| 50 | 85 | 5 | 70 | 0 | 90 | — | 100 | 0 |
| 51 | 85 | 10 | 85 | 0 | 100 | — | 100 | 5 |
| 52 | 100 | 80 | 100 | 100 | 100 | — | 100 | 85 |
| 55 | 100 | 100 | 100 | 100 | 100 | — | 100 | 100 |
| 56 | 0 | 0 | 0 | 0 | 0 | — | 0 | 0 |
| 59 | 100 | 100 | 100 | 100 | 100 | — | 100 | 100 |
| 60 | 10 | 5 | 5 | 20 | 10 | — | 100 | 0 |
| 61 | 15 | 10 | 0 | 10 | 20 | — | 70 | 0 |
| 62 | 85 | 40 | 80 | 80 | 90 | — | 100 | 5 |
| 63 | 100 | 50 | 40 | 100 | 100 | — | 100 | 40 |
| 64 | 100 | 80 | 100 | 100 | 100 | — | 100 | 65 |
| 65 | 100 | 80 | 100 | 100 | 100 | — | 100 | 50 |
| 66 | 85 | 60 | 85 | 100 | 100 | — | 100 | 15 |
| 67 | 100 | 5 | 100 | 40 | 100 | — | 100 | 5 |
| 73 | 100 | 25 | 100 | 100 | 100 | — | 100 | 5 |
| 74 | 100 | 15 | 100 | 100 | 100 | — | 100 | 5 |
| 75 | 100 | 5 | 100 | 0 | 100 | — | 100 | 0 |
| 76 | 100 | 5 | 70 | 60 | 100 | — | 100 | 5 |
| 78 | 100 | 10 | 25 | 100 | 100 | — | 100 | 5 |
| 80 | 40 | 15 | 5 | 100 | 100 | — | 100 | 5 |
| 81 | 80 | 75 | 90 | 100 | 100 | — | 100 | 10 |
| 82 | 0 | 0 | 0 | 10 | 0 | — | 0 | 0 |
| 83 | 0 | 0 | 0 | 0 | 0 | — | 0 | 0 |
| 85 | 20 | 10 | 15 | 100 | 100 | — | 100 | 5 |
| 87 | 60 | 5 | 10 | 100 | 100 | — | 100 | 10 |
| 92 | 100 | 50 | 100 | 100 | 100 | — | 100 | 5 |
| 93 | 100 | 5 | 98 | 0 | 98 | — | 100 | 0 |
| 94 | 100 | 60 | 100 | 100 | 100 | — | 100 | 10 |
| 101 | 60 | 5 | 5 | 60 | 100 | — | 100 | 0 |
| 102 | 85 | 10 | 10 | 100 | 100 | — | 100 | 0 |
| 107 | 0 | 0 | 0 | 0 | 0 | — | 0 | 0 |
| 108 | 0 | 0 | 0 | 0 | 0 | — | 0 | 0 |
| 109 | 0 | 0 | 0 | 0 | 0 | — | 0 | 0 |
| 110 | 10 | 5 | 5 | 40 | 80 | — | 100 | 0 |
| 112 | 0 | 0 | 0 | 0 | 0 | — | 0 | — |
| 113 | 0 | 0 | 0 | 0 | 0 | — | 0 | 0 |
| 114 | 10 | 0 | 0 | 15 | 10 | — | 5 | 0 |
| 115 | 50 | 20 | 30 | 100 | 90 | — | 30 | 20 |
| 116 | 0 | 0 | 0 | 0 | 5 | — | 5 | 0 |
| 117 | 50 | 5 | 10 | 25 | 100 | — | 90 | 5 |
| 118 | 10 | 0 | 5 | 30 | 15 | — | 15 | 0 |
| 122 | 75 | 10 | 85 | 15 | 100 | — | 20 | 10 |
| 123 | 85 | 5 | 10 | 0 | 100 | — | 100 | 5 |
| 125 | 95 | 5 | 20 | 90 | 100 | — | 100 | 5 |
| 126 | 75 | 5 | 10 | 25 | 85 | — | 75 | 0 |
| 127 | 30 | 5 | 10 | 100 | 100 | — | 100 | 0 |
| 143 | 60 | 5 | 15 | 85 | 100 | — | 100 | 5 |
| 144 | 10 | 5 | 5 | 60 | 50 | — | 60 | 0 |
| 145 | 15 | 0 | 0 | 80 | 10 | — | 50 | 0 |
| 146 | 50 | 10 | 5 | 5 | 95 | — | 100 | 0 |
| 147 | 70 | 20 | 25 | 98 | 95 | — | 100 | 5 |
| 148 | 10 | 0 | 0 | 60 | 15 | — | 5 | 0 |
| 158 | 10 | 0 | 0 | 70 | 100 | — | 70 | 0 |
| 159 | 40 | 5 | 5 | 100 | 100 | — | 100 | 5 |
| 161 | 10 | 5 | 5 | 90 | 75 | — | 60 | 5 |
| 162 | 90 | 100 | 100 | 98 | 100 | — | 100 | 40 |
| 163 | 0 | 0 | 0 | 10 | 0 | — | 5 | 0 |
| 168 | 5 | 5 | 0 | 40 | 60 | — | 40 | 0 |
| 169 | 10 | 0 | 0 | 5 | 30 | — | 25 | 0 |
| 170 | 0 | 0 | 0 | 10 | 5 | — | 5 | 0 |
| 181 | 95 | 10 | 25 | 100 | 100 | — | 100 | 5 |
| 184 | 25 | 5 | 10 | 25 | 5 | — | 10 | 0 |
| 204 | 60 | 0 | 0 | 50 | 100 | — | 100 | 5 |
| 205 | 98 | 5 | 60 | 60 | 100 | — | 100 | 5 |
| 211 |  | 30 | 80 | 100 | 100 | — | 100 | 5 |
| 212 |  | 98 | 100 | 100 | 100 | — | 100 | 50 |

TABLE IV-continued

Post-emergence Herbicidal Activity
Application Rate -- 4.0 kg/ha

| CMPD. NO. | SETVI | AVEFA | ECHCG | SINAR | ABUTH | PHBPU | IPOSS | CYPES |
|---|---|---|---|---|---|---|---|---|
| 213 |  | 70 | 70 | 5 | 100 | — | 100 | 5 |
| 215 | 80 | 80 | 50 | 100 | 100 | — | 100 | 5 |
| 216 | 50 | 15 | 20 | 5 | 100 | — | 100 | 5 |
| 217 | 100 | 60 | 100 | 100 | 100 | — | 100 | 75 |
| 218 | 100 | 75 | 100 | 100 | 100 | — | 100 | 80 |
| 223 | 15 | 0 | 0 | 40 | 100 | — | 100 | 0 |
| 224 | 100 | 90 | 100 | 100 | 100 | — | 100 | 100 |
| 225 | 20 | 0 | 5 | 0 | 30 | — | 10 | 0 |
| 228 | 100 | 15 | 100 | 100 | 100 | — | 100 | 15 |
| 229 | 100 | 10 | 100 | 100 | 100 | — | 100 | 5 |
| 230 | 50 | 5 | 5 | 50 | 100 | — | 100 | 5 |
| 231 | 5 | 0 | 0 | 5 | 50 | — | 50 | 0 |
| 232 | 10 | 0 | 0 | 25 | 25 | — | 150 | 0 |
| 233 | 100 | 95 | 60 | 100 | 100 | — | 100 | 100 |
| 234 | 10 | 5 | 5 | 100 | 100 | — | 100 | 0 |
| 238 | 100 | 10 | 90 | 100 | 100 | — | 100 | 5 |
| 239 | 90 | 10 | 30 | 70 | 100 | — | 100 | 0 |
| 240 | 80 | 10 | 30 | 30 | 100 | — | 100 | 10 |
| 241 | 80 | 10 | 25 | 10 | 100 | — | 100 | 10 |
| 244 | 100 | 25 | 98 | 95 | 100 | — | 100 | 20 |
| 251 | 100 | 10 | 100 | 25 | 100 | — | 100 | 5 |
| 252 | 50 | 5 | 5 | 25 | 100 | — | 100 | 0 |

TABLE V

Post-emergence Herbicidal Activity
Application Rate - 1.0 kg/ha

| CMPD. NO. | SETVI | AVEFA | ECHCG | SINAR | ABUTH | PHBPU | IPOSS | CYPES |
|---|---|---|---|---|---|---|---|---|
| 1 | 100 | 0 | 0 | 80 | 100 | 100 | — | 0 |
| 2 | 100 | 60 | 100 | 100 | 100 | 100 | — | 0 |
| 3 | 100 | 0 | 0 | 0 | 0 | 0 | — | 0 |
| 4 | 100 | 0 | 0 | 0 | 0 | 0 | — | 0 |
| 5 | 0 | 0 | 0 | 0 | 0 | 0 | — | 0 |
| 59 | 100 | 100 | 100 | 100 | 100 | — | 100 | 95 |
| 68 | 100 | 5 | 100 | 100 | 100 | — | 100 | 30 |
| 69 | 80 | 10 | 20 | 100 | 100 | — | 100 | 5 |
| 70 | 70 | 15 | 40 | 100 | 100 | — | 100 | 15 |
| 71 | 60 | 10 | 10 | 100 | 100 | — | 100 | 10 |
| 72 | 40 | 10 | 20 | 100 | 100 | — | 100 | 20 |
| 77 | 95 | 60 | 95 | 100 | 100 | — | 100 | 15 |
| 79 | 100 | 20 | 75 | 100 | 100 | — | 100 | 40 |
| 84 | 10 | 5 | 5 | 100 | 100 | — | 100 | 15 |
| 86 | 90 | 60 | 90 | 100 | 100 | — | 100 | 30 |
| 88 | 60 | 60 | 20 | 100 | 100 | — | 100 | 20 |
| 89 | 25 | 10 | 20 | 100 | 100 | — | 100 | 10 |
| 90 | 15 | 10 | 5 | 100 | 100 | — | 100 | 5 |
| 91 | 100 | 70 | 95 | 100 | 100 | — | 100 | 30 |
| 95 | 85 | 5 | 75 | 15 | 100 | — | 100 | 0 |
| 96 | 85 | 10 | 30 | 100 | 100 | — | 100 | 5 |
| 97 | 100 | 0 | 95 | 30 | 100 | — | 100 | 15 |
| 98 | 100 | 0 | 30 | 100 | 100 | — | 100 | 15 |
| 99 | 80 | 10 | 10 | 100 | 90 | — | 100 | 10 |
| 100 | 75 | 5 | 15 | 0 | 70 | — | 100 | 5 |
| 103 | 80 | 5 | 10 | 85 | 100 | — | 100 | 10 |
| 104 | 90 | 5 | 20 | 5 | 100 | — | 100 | 10 |
| 105 | 40 | 5 | 5 | 15 | 100 | — | 100 | 5 |
| 106 | 60 | 5 | 5 | 90 | 100 | — | 85 | 5 |
| 111 | 60 | 10 | 30 | 100 | 100 | — | 100 | 5 |
| 119 | 100 | 50 | 100 | 100 | 100 | — | 100 | 5 |
| 120 | 100 | 10 | 85 | 100 | 100 | — | 100 | 5 |
| 121 | 10 | 5 | 5 | 60 | 100 | — | 100 | 0 |
| 124 | 85 | 10 | 15 | 100 | 100 | — | 100 | 5 |
| 128 | 100 | 25 | 100 | 100 | 100 | — | 100 | 5 |
| 129 | 75 | 15 | 75 | 100 | 100 | — | 100 | 5 |
| 130 | 10 | 0 | 5 | 60 | 50 | — | 60 | 0 |
| 131 | 90 | 20 | 25 | 30 | 75 | — | 100 | 5 |
| 132 | 100 | 98 | 100 | 100 | 100 | — | 100 | 25 |

TABLE V-continued

Post-emergence Herbicidal Activity
Application Rate - 1.0 kg/ha

| CMPD. NO. | SETVI | AVEFA | ECHCG | SINAR | ABUTH | PHBPU | IPOSS | CYPES |
|---|---|---|---|---|---|---|---|---|
| 133 | 60 | 80 | 60 | 100 | 100 | — | 100 | 65 |
| 134 | 50 | 15 | 40 | 100 | 100 | — | 100 | 25 |
| 135 | 100 | 100 | 100 | 100 | 100 | — | 100 | 80 |
| 136 | 95 | 50 | 75 | 100 | 100 | — | 100 | 10 |
| 137 | 30 | 85 | 20 | 100 | 100 | — | 100 | 20 |
| 138 | 85 | 80 | 30 | 100 | 100 | — | 100 | 25 |
| 139 | 95 | 50 | 100 | 100 | 100 | — | 100 | 35 |
| 140 | 60 | 75 | 95 | 100 | 100 | — | 100 | 25 |
| 141 | 100 | 100 | 100 | 100 | 100 | — | 100 | 75 |
| 142 | 100 | 10 | 90 | 100 | 100 | — | 100 | 5 |
| 150 | 10 | 0 | 5 | 60 | 100 | — | 85 | 5 |
| 151 | 70 | 5 | 5 | 100 | 100 | — | 100 | 20 |
| 152 | 100 | 10 | 5 | 100 | 100 | — | 100 | 15 |
| 153 | 100 | 100 | 100 | 100 | 100 | — | 100 | 85 |
| 154 | 100 | 100 | 100 | 100 | 100 | — | 100 | 98 |
| 155 | 100 | 50 | 30 | 100 | 100 | — | 100 | 5 |
| 156 | 60 | 10 | 10 | 100 | 100 | — | 100 | 10 |
| 157 | 100 | 100 | 100 | 100 | 100 | — | 100 | 70 |
| 160 | 100 | 15 | 95 | 5 | 100 | — | 100 | 10 |
| 164 | 100 | 100 | 100 | 100 | 100 | — | 100 | 98 |
| 165 | 85 | 100 | 30 | 100 | 100 | — | 100 | 60 |
| 166 | 100 | 100 | 100 | 100 | 100 | — | 100 | 80 |
| 167 | 98 | 30 | 90 | 80 | 100 | — | 100 | 5 |
| 171 | 100 | 100 | 100 | 100 | 100 | — | 100 | 60 |
| 172 | 30 | 10 | 10 | 100 | 100 | — | 100 | 5 |
| 173 | 10 | 5 | 5 | 90 | 95 | — | 100 | 5 |
| 174 | 100 | 100 | 100 | 100 | 100 | — | 100 | 60 |
| 175 | 90 | 25 | 60 | 100 | 100 | — | 100 | 10 |
| 176 | 95 | 100 | 100 | 100 | 100 | — | 100 | 40 |
| 177 | 100 | 70 | 50 | 100 | 100 | — | 95 | 25 |
| 178 | 100 | 100 | 100 | 100 | 100 | — | 100 | 30 |
| 179 | 100 | 100 | 100 | 100 | 100 | — | 100 | 60 |
| 180 | 100 | 100 | 100 | 100 | 100 | — | 100 | 70 |
| 182 | 70 | 10 | 30 | 15 | 100 | — | 90 | 0 |
| 183 | 95 | 5 | 20 | 70 | 100 | — | 98 | 5 |
| 185 | 100 | 100 | 100 | 100 | 100 | — | 100 | 95 |
| 186 | 75 | 20 | 20 | 100 | 100 | — | 100 | 20 |
| 187 | 85 | 20 | 15 | 70 | 90 | — | 100 | 5 |
| 188 | 100 | 100 | 100 | 100 | 100 | — | 100 | 70 |
| 189 | 100 | 100 | 100 | 100 | 100 | — | 100 | 75 |
| 190 | 100 | 75 | 100 | 90 | 100 | — | 100 | 30 |
| 191 | 100 | 100 | 100 | 100 | 100 | — | 100 | 40 |
| 192 | 100 | 100 | 100 | 100 | 100 | — | 100 | 40 |
| 193 | 100 | 80 | 100 | 100 | 100 | — | 100 | 60 |
| 194 | 70 | 30 | 70 | 100 | 100 | — | 100 | 20 |
| 195 | 90 | 30 | 60 | 50 | 100 | — | 100 | 15 |
| 196 | 60 | 10 | 15 | 90 | 100 | — | 100 | 10 |
| 197 | 100 | 60 | 60 | 100 | 100 | — | 100 | 5 |
| 198 | 30 | 5 | 15 | 100 | 100 | — | 100 | 5 |
| 199 | 30 | 10 | 15 | 85 | 100 | — | 100 | 5 |
| 200 | 30 | 5 | 5 | 80 | 100 | — | 100 | 5 |
| 201 | 100 | 80 | 75 | 100 | 100 | — | 100 | 50 |
| 202 | 100 | 5 | 100 | 95 | 100 | — | 100 | 15 |
| 203 | 70 | 60 | 70 | 100 | 100 | — | 100 | 5 |
| 206 | 98 | 100 | 100 | 100 | 100 | — | 100 | 30 |
| 207 | 100 | 95 | 100 | 100 | 100 | — | 100 | 25 |
| 208 | 100 | 98 | 85 | 50 | 40 | — | 100 | 50 |
| 209 | 100 | 85 | 75 | 75 | 100 | — | 100 | 85 |
| 210 | 100 | 75 | 100 | 100 | 100 | — | 100 | 85 |
| 214 |  | 85 | 85 | 100 | 100 | — | 100 | 20 |
| 219 | 95 | 10 | 40 | 0 | 100 | — | 100 | 10 |
| 220 | 10 | 0 | 0 | 10 | 30 | — | 15 | 0 |
| 221 | 100 | 100 | 100 | 100 | 100 | — | 100 | 40 |
| 222 | 100 | 15 | 100 | 100 | 100 | — | 100 | 5 |
| 226 | 100 | 15 | 80 | 100 | 100 | — | 100 | 0 |
| 227 | 100 | 10 | 100 | 5 | 100 | — | 100 | 10 |
| 235 | 100 | 90 | 100 | 100 | 100 | — | 100 | 30 |
| 236 | 100 | 15 | 15 | 100 | 100 | — | 100 | 10 |
| 237 | 90 | 5 | 5 | 5 | 100 | — | 100 | 10 |
| 242 | 100 | 20 | 70 | 100 | 100 | — | 100 | 30 |
| 243 | 100 | 100 | 100 | 100 | 100 | — | 100 | 60 |
| 245 | 100 | 95 | 100 | 100 | 100 | — | 100 | 60 |
| 246 | 100 | 100 | 100 | 100 | 100 | — | 100 | 70 |

TABLE V-continued

Post-emergence Herbicidal Activity
Application Rate - 1.0 kg/ha

| CMPD. NO. | SETVI | AVEFA | ECHCG | SINAR | ABUTH | PHBPU | IPOSS | CYPES |
|---|---|---|---|---|---|---|---|---|
| 247 | 100 | 98 | 100 | 100 | 100 | — | 100 | 75 |
| 248 | 10 | 5 | 5 | 20 | 50 | — | 50 | 5 |
| 249 | 100 | 75 | 100 | 100 | 100 | — | 100 | 40 |
| 250 | 75 | 5 | 10 | 100 | 100 | — | 100 | 10 |
| 255 | 100 | 100 | 100 | 100 | 100 | — | 100 | 100 |

The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Such formulations may contain in addition to the active compound various carriers or diluents; wetting, dispersing or emulsifying agents' solvents (water, or organic solvents such as aromatic solvents or chlorinated aliphatic solvents); adhesives; thickeners and other substances. Examples of surface active agents are alkyl and alkylaryl sulfonates and sulfates and their salts; polyhydric alcohols; polyethoxylated alcohols; esters and fatty amines. These agents when used normally comprise from 0.1% to 15% by weight of the formulation.

The compounds of the present invention are also useful when combined with other herbicides and/or defoliants, dessicants, growth inhibitors, insecticdes, fungicides, nematocides, and the like. These other materials can comprise from about 5% to about 95% of the active ingredients in the formulations. These combinations frequently provided a higher level of effectiveness in controlling weeds and often provide results unattainable with separate formulations of the individual herbicides. The compositions may contain as well as other pesticides, also fertilizers, all intended for and formulated for use at the same locus.

Examples of other herbicides, defoliants, dessicants and plant growth inhibitors with which the compounds of this invention can be combined are:

Examples of useful complementary herbicides include:

A. Benzo-2,1,3-thiodiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron and methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimethametryn, simetryne and terbutryn;

K. phosphorothioate herbicides such as piperophos, bensulide and butamifos;

L. thiolcarbamate herbicides such as cycloate, vernolate, molinate, thiobencarb, butylate, EPTC, triallate, diallate, ethyl esprocarb, tiocarbazil, pyridate and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, alachlor, propachlor, propanil, metazachlor, metolachlor, acetochlor and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, tralkoxydim and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and gluyfosinate and their salts and esters, sulphosate and bilanafos;

Y. organoarsenical herbicides such as MSMA;

Z. herbicidal amide derivative such as napropamide, propyzamide, carbetamide, tebutam, bromobutide, isoxaben, naproanilide, diphenamid and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

These formulations can be applied to the areas where control is desired by conventional methods. Dust and liquid compositions, for example, can be applied by the use of powerdusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

| | |
|---|---|
| 5% dust: | 5 parts active compound |
| | 95 parts talc |
| 2% dust | 2 parts active compound |
| | 1 part highly dispersed silicic acid |
| | 97 parts talc |

These dusts are formed by mixing the components then grinding the mixture to the desired particle size.

| | |
|---|---|
| 5% granules: | 5 parts active compound |
| | 0.25 part epichlorohydrin |
| | 0.25 part cetyl polyglycol ether |
| | 3.5 parts polyethylene glycol |
| | 91 part kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo. Wettable powders:

| | | |
|---|---|---|
| 70%: | 70 | parts active compound |
| | 5 | parts sodium dibutylnaphthylsulfonate |
| | 3 | parts naphthalenesulfonic acid/phenolsulfonic acid/formaldehyde condensate (3:2:1) |
| | 10 | parts kaolin |
| | 12 | parts Champagne chalk |
| 40%: | 40 | parts active compound |
| | 5 | parts sodium lignin sulfonate |
| | 1 | part sodium dibutylnaphthalene sulfonic acid |
| | 54 | parts silicic acid |
| 25%: | 25 | parts active compound |
| | 4.5 | parts calcium lignin sulfate |
| | 1.9 | parts Champagne chalk/hydroxyethyl cellulose (1:1) |
| | 1.5 | parts sodium dibutylnaphthalene sulfonate |
| | 19.5 | silicic acid |
| | 19.5 | parts Champagne chalk |
| | 28.1 | parts kaolin |
| 25%: | 25 | parts active compound |
| | 2.5 | parts isooctylphenoxy-polyethylene-ethanol |
| | 1.7 | parts Champagne chalk/hydroxyethyl cellulose (1:1) |
| | 8.3 | parts sodium aluminum silicate |
| | 16.5 | parts kieselguhr |
| | 46 | parts kaolin |
| 10%: | 10 | parts active compound |
| | 3 | parts of a mixture of sodium salts of saturated fatty alcohol sulfates |
| | 5 | parts naphthalenesulfonic acid/ formaldehyde condensate |
| | 82 | parts kaolin |

These wettable powders are prepared by intimately mixing the active compounds with the additives in suitable mixers, and grinding the resulting mixture in mills or rollers.
Emulsifiable concentrate:

| | | |
|---|---|---|
| 25%: | 25 | parts active compound |
| | 2.5 | parts epoxidized vegetable oil |
| | 10 | parts of an alkylarylsulfonate/fatty alcohol polyglycol ether mixture |
| | 5 | parts dimethylformamide |
| | 57.5 | parts xylene |
| 50% | 50 | parts active compound |
| | 45 | parts kerosene |
| | 5 | parts emulsifying agent (mixture of long chain estroxylated polyetheis with long chain sulfonate |

What is claimed is:
1. A compound having the formula

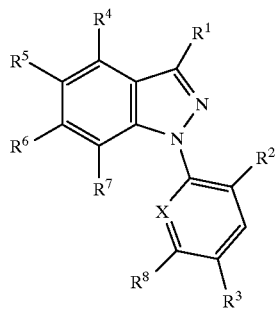

wherein $R^1$ is halogen;

$R^2$ is hydrogen; nitro; halogen; alkyl; cyano; alkylthio; alkylsulfinyl; alkylsulfonyl; alkoxy; acetylamino; or amino;

$R^3$ is hydrogen; halogen; haloalkyl; haloalkoxy; cyano; amino or $SO_yR^{13}$ and $R^{13}$ is alkyl or haloalkyl and y is 0, 1, or 2.

$R^4$, $R^5$ and $R^6$ are independently selected from the group consisting of hydrogen; halogen; nitro; hydroxy; cyano; alkyl; alkoxyiminoalkyl; hydroxyalkyl; alkoxyalkyl; alkylsulfonylaminoalkyl; haloalkylsulfonylaminoalkyl; (alkyl)$_n$aminoalkyl; (alkylcarbonyloxy)$_z$alkyl; haloalkyl; formyl; alkylcarbonyl; carboxy and its salts; COOalkyl; carboxamido; substituted carboxamido wherein the nitrogen substituents are selected from alkyl, haloalkylsulfonyl, and alkylsulfonyl; sulfonamido; substituted sulfonamido wherein the nitrogen has an alkyl substituent; (alkylsulfonyl)$_z$amino; (acetyl)$_z$amino; or $YR^9$ wherein Y is O, $NR^{12}$, or $S(O)_n$;

$R^9$ is —(R$^{11}$)$_m$—COR$^{10}$; —(R$^{11}$)$_m$—SO$_2$R$^{10}$; alkyl; haloalkyl; hydroxyalkyl; aralkyl; cyanoalkyl; acetoxyalkyl; alkoxyalkyl; alkenyl; or alkynyl;

$R^{10}$ is alkyl; haloalkyl; hydrogen; hydroxy; alkoxy; alkoxyalkyl; alkoxyalkoxy; alkoxyalkylamino; dialkoxyalkylamino; aryloxy; aralkyl; alkoxycarbonyl; hydroxycarboxyl; alkoxycarbonylalkyl; hydroxycarbonylalkyl; (alkyl)$_n$amino; (alkyl)$_n$hydrazino; alkoxycarbonylalkylamino; hydroxyalkylarnino; (alkyl)$_n$aminoalkylamino; (alkyl)$_n$aminocarbonylalkylamino; hydroxycarbonylalkylamino; alkylsulfonylamino; arylsulfonylamino; acetylaminoalkylamino; N-alkoxy-N-(alkyl)$_m$amino; N-hydroxy-N-(alkyl)$_m$amino; cyanoalkylamino; (alkenyl)$_n$amino; alkoxyalkylamino; (alkynyl)$_n$amino; alkenyloxy; alkynyloxy; or semicarbazido;

$R^{11}$ is alkylene;

$R^{12}$ is hydrogen; alkyl; alkenyl; alkynyl or alkylcarbonyl;

m is 0 or 1;

n is 0,1 or2;

z is 1 or 2;

$R^7$ is hydrogen; halogen; alkyl; or nitro;

$R^8$ is hydrogen or halogen;

X is $CR^{14}$ wherein $R^{14}$ is hydrogen; halogen; haloalkyl; cyano; or nitro; with a proviso that only one or two electron withdrawing groups are present with respect to the terms $R^4$, $R^5$ and $R^6$;

or an agriculturally acceptable salt thereof.

2. A compound according to claim 1 wherein $R^2$ is hydrogen, halogen, alkyl, alkylthio or alkoxy; $R^3$ is hydrogen, halogen, $SO_yR^{13}$ or haloalkyl; $R^4$, $R^5$ and $R^6$ are independently hydrogen, cyano, halogen, alkyl, nitro, alkoxy, haloalkyl, carboxy and its salts, COOalkyl, a substituted carboxamido, carboxamido, sulfonamido, substituted sulfonamido and $YR^9$ wherein Y is O, $NR^{12}$, or $S(O)_n$; $R^9$ is —(R$^{11}$)$_m$—COR$^{10}$; —(R$^{11}$)$_m$—SO$_2$R$^{10}$; alkyl, haloalkyl, cyanoalkyl, alkoxyalkyl, alkenyl, or alkynyl; $R^7$ is hydrogen or halogen and X CR$^{14}$ wherein $R^{14}$ is halogen.

3. A compound according to claim 1 wherein $R^4$, $R^5$ and $R^6$ are independently hydrogen, halogen, alkyl and $YR^9$ wherein Y is O; and $R^9$ is —(R$^{11}$)$_m$—COR$^{10}$; —(R$^{11}$)$_m$—SO$_2$R$^{10}$; alkyl; haloalkyl; hydroxyalkyl; aralkyl; cyanoalkyl; acetoxyalkyl; alkoxyalkyl; hydroxy; alkenyl; or alkynyl, and $R^{11}$ is —CH$_2$—, —CH(CH$_3$)— and —CH$_2$CH$_2$—.

4. A compound according to claim 3 wherein X is C-halogen.

5. A compound according to claim 3 wherein $R^4$ is hydrogen.

6. A compound according to claim 3 wherein $R^4$ and $R^5$ are hydrogen.

7. A compound according to claim 2 wherein $R^2$ is hydrogen or halogen; $R^3$ is haloalkyl; $R^4$ is hydrogen; $R^5$ is hydrogen; $R^6$ is $YR^9$; $R^7$ is hydrogen; $R^8$ is hydrogen and X is C-halogen.

8. A compound according to claim 7 wherein X is C-halogen.

9. A compound according to claim 7 wherein $R^6$ is $O(R^{11})_m COR^{10}$.

10. A compound according to claim 9 wherein $R^{10}$ is hydrogen, alkoxy; alkoxyalkyl; alkoxyalkoxy; alkoxyalkylamino; dialkoxyalkylamino; alkoxycarbonyl; $(alkyl)_n$ amino; alkoxycarbonylalkylamino; $(alkyl)_n$ aminoalkylamino.

11. A compound according to claim 1 wherein $R^4$, $R^5$ and $R^6$ are independently hydrogen, halogen, alkyl, cyano, haloalkyl and $YR^9$ wherein Y is O, $NR^{12}$ or $S(O)_n$.

12. A compound according to claim 11 wherein $R^4$ is hydrogen, halogen, alkyl, cyano, haloalkyl and alkoxy; $R^5$ is hydrogen and X is C-halogen.

13. A compound according to claim 1 wherein $R^6$ is $YR^9$ wherein Y is O and $NR^{12}$ or an agriculturally acceptable salt thereof.

14. A compound according to claim 11 wherein $R^2$ is hydrogen or halogen; $R^3$ is haloalkyl; $R^4$ is hydrogen; $R^5$ is hydrogen; $R^7$ is hydrogen; $R^8$ is hydrogen, and X is C-halogen.

15. A compound according to claim 14 wherein $R^6$ is $NR^{12}$.

16. A compound according to claim 1 wherein $R^1$, $R^4$, $R^5$, $R^7$ and $R^8$ are hydrogen; $R^2$ is hydrogen or halogen and $R^3$ is haloalkyl.

17. A compound according to claim 13 wherein X is C-halogen.

18. A compound according to claim 14 wherein X is C-chloro.

19. A compound according to claim 1 wherein $R^4$ $R^5$ and $R^6$ are independently hydrogen.

20. A compound according to claim 16 wherein $R^2$ is hydrogen or halogen; $R^3$ is haloalkyl; $R^7$ is hydrogen; $R^8$ is hydrogen and X is C-halogen.

21. A compound according to claim 1 wherein $R^1$ is hydrogen; $R^2$ is halogen; $R^3$ is haloalkyl; $R^4$ is hydrogen; $R^5$ is hydrogen; $R^7$ is hydrogen; $R^8$ is hydrogen and X is C-halogen.

22. A compound according to claim 17 wherein X is C-chloro.

23. A compound according to claim 1 wherein $R^1$, $R^7$ and $R^8$ are hydrogen; $R^2$ is hydrogen or halogen; $R^4$, $R^5$ and $R^6$ are hydrogen or $YR^9$; $R^3$ is haloalkyl or $SO_yR^{13}$ and X is C-chloro.

24. A compound according to claim 19 wherein $R^3$ is $CF_3$.

25. A compound according to claim 1 wherein $R^4$ is hydrogen, halogen, alkyl, cyano and alkoxy.

26. A compound according to claim 1 wherein $R^1$, $R^7$ and $R^8$ are hydrogen; $R^2$ is hydrogen or halogen; $R^3$ is haloalkyl; $R^4$ is hydrogen, methyl, methoxy, chloro, bromo, fluoro, and cyano, and X is C-halogen.

27. A compound according to claim 21 wherein $R^2$ is hydrogen or chloro; $R^3$ is $CF_3$; $R^5$ is hydrogen; $R^6$ is hydrogen and X is C-chloro.

28. A compound according to claim 1 wherein $R^5$ is selected from hydrogen, nitro, halogen, cyano, alkyl, carboxy and its salt, haloalkyl, COOalkyl, alkyl substituted sulfonamido, substituted carboxamido, formyl, and $YR^9$ in which Y is O and $NR^{12}$; $R^9$ is alkyl, alkenyl, alkynyl, $(R^{11})_m$—$COR^{10}$ and $R^{12}$ is hydrogen or alkyl.

29. A compound according to claim 28 wherein $R^1$ is hydrogen; $R^2$ is hydrogen or halogen; $R^3$ is haloalkyl; $R^4$ is hydrogen; $R^6$ is hydrogen, halogen alkyl or $YR^9$; $R^7$ is hydrogen; $R^8$ is hydrogen and X is C-halogen.

30. A compound according to claim 28 wherein $R^5$ is hydrogen, nitro, chloro, bromo, fluoro, methyl, cyano, formyl, —$CHF_2$ and $CF_3$.

31. A compound according to claim 24 wherein $R^1$ is hydrogen; $R^2$ is hydrogen or halogen; $R^3$ is haloalkyl; $R^4$, $R^7$ and $R^8$ are hydrogen; $R^6$ is $YR^9$ and X is C-halogen.

32. A compound according to claim 25 wherein $R^6$ is $OR^9$.

33. A compound according to claim 1 wherein $R^1$, $R^4$, $R^5$, $R^7$ and $R^8$ are hydrogen; $R^2$ is hydrogen or halogen; $R^3$ is $CF_3$; X is C-chloro and $R^6$ is $OR^9$.

34. A compound according to claim 27 wherein $R^9$ is

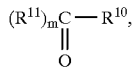

alkyl and alkoxyalkyl.

35. A compound according to claim 34 wherein $R^{11}$ is —$CH_2$—, —$CH_2CH_2$— and —$CH(CH_3)$— and m is 1.

36. A compound according to claim 34 wherein $R^{10}$ is $OCH_3$, $NHNH_2$, $NHOCH_3$, $NHN=C(CH_3)_2$,

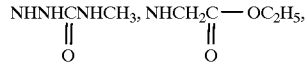

$NHCH_2CH_2OH$, $NHCH_2CH_2OCH_3$,

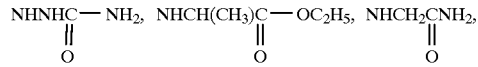

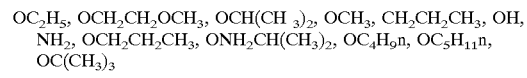

and

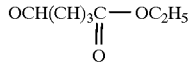

or an agriculturally acceptable salt thereof.

37. A compound according to claim 36 wherein the agriculturally acceptable salts include ammonium, potassium, sodium, nitrate, sulfate and hydrochloride.

38. A compound according to claim 33 wherein $R^6$ is

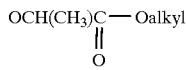

and X is C-chloro.

39. A compound according to claim 1 wherein $R^2$ is hydrogen; $R^3$ is $CF_3$; $R^4$ is hydrogen; $R^5$ is hydrogen; $R^6$ is

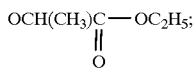

$R^7$ is hydrogen; $R^8$ is hydrogen and X is C-chloro.

40. A compound according to claim 1 wherein $R^2$ is chloro; $R^3$ is $CF_3$; $R^4$ is hydrogen; $R^5$ is fluoro; $R^6$ is $OCH_3$; $R^7$ is hydrogen; $R^8$ is hydrogen and X is C-chloro.

41. A method of controlling undesirable vegetation comprising applying to such vegetation or the locus thereof, a herbicidally effective amount of a compound according to claim 1.

42. A method according to claim 41 wherein $R^1$ is hydrogen; $R^2$ is hydrogen or halogen; $R^3$ is hydrogen, halogen, $SO_yR^{13}$, or haloalkyl; $R^4$, $R^5$ and $R^6$ are independently hydrogen, halogen, alkyl, cyano, haloalkyl and $YR^9$; $R^7$ is hydrogen, and X is $CR^{14}$ wherein $R^{14}$ is hydrogen, halogen or haloalkyl.

43. A method according to claim 41 wherein $R^3$ is haloalkyl; $R^4$ is hydrogen, halogen, alkyl, cyano, haloalkyl and alkoxy; $R^5$ is hydrogen; $R^6$ is $YR^9$ wherein Y is O and $NR^{13}$ and X is C-halogen.

44. A method according to claim 41 wherein $R^3$ is haloalkyl; $R^4$ is hydrogen; $R^5$ is hydrogen, halogen, alkyl, cyano, haloalkyl and alkoxy; $R^6$ is $YR^9$ wherein Y is O and $NR^{13}$ and X is C-halogen.

45. A herbicidal composition of matter comprising a) A herbicidally effective amount of a compound according to claim 1, and;

b) A diluent or carrier suitable for use with herbicides.

46. A compound according to claim 1 wherein X is C-Cl; $R^2$ is chlorine; $R^3$ is trifluoromethyl; $R^4$, $R^5$, $R^7$ and $R^8$ are hydrogen; and $R^6$ is $OCH(CH_3)CO_2C_2H_5$.

* * * * *